United States Patent
Sallman et al.

(10) Patent No.: US 8,008,023 B2
(45) Date of Patent: Aug. 30, 2011

(54) NATURAL LIGAND OF G PROTEIN COUPLED RECEPTOR RCC356 AND USES THEREOF

(75) Inventors: Frédéric Sallman, Brussel (BE); Alex Veithen, Houtain-le-Val (BE); Magali Philippeau, Wemmel (BE)

(73) Assignee: Chemcom S.A., Brussels (BE)

( * ) Notice: Subject to any disclaimer, the term of this patent is extended or adjusted under 35 U.S.C. 154(b) by 474 days.

(21) Appl. No.: 12/152,275

(22) Filed: May 12, 2008

(65) Prior Publication Data
US 2009/0264526 A1    Oct. 22, 2009

Related U.S. Application Data

(63) Continuation of application No. 11/897,793, filed on Aug. 30, 2007, now abandoned, which is a continuation of application No. PCT/EP2006/001904, filed on Mar. 2, 2006.

(30) Foreign Application Priority Data

Mar. 3, 2005 (EP) .................................. 05447046

(51) Int. Cl.
*G01N 33/53* (2006.01)
*C07K 14/00* (2006.01)
(52) U.S. Cl. ........................................ 435/7.1; 530/350

(58) Field of Classification Search .................. None
See application file for complete search history.

(56) References Cited

U.S. PATENT DOCUMENTS

2003/0105000 A1* 6/2003 Pero et al. ........................ 514/12
2004/0005563 A1* 1/2004 Mack et al. ........................ 435/6

OTHER PUBLICATIONS

Bowie et al. (Science, 1990, 247:1306-1310).*
Skolnick et al. (Tibtech 18:34-39, 2000).*
Ibragimova and Eade (Biophysical Journal, Oct 1999, vol. 77, pp. 2191-2198).*
Burgess et al. (J of Cell Bio. 111:2129-2138, 1990).*
Lazar et al. (Molecular and Cellular Biology, 1988, 8:1247-1252).*
Scott et al. (Nature Genetics, 1999, 21:440-443).*
NCBI Ref. Seq. NP_689643 (olfactory receptor 51E1, gi: 205277378, Mar. 2010).*

* cited by examiner

*Primary Examiner* — Peter J Reddig
(74) *Attorney, Agent, or Firm* — Edwards Angell Palmer & Dodge LLP; Kathleen Williams; Amy DeCloux

(57) ABSTRACT

The invention relates to the identification of isovaleric acid as a natural ligand of the RCC356 G-protein coupled receptor (GPCR). The invention encompasses the use of the interaction of RCC356 polypeptides and isovaleric acid as the basis of screening assays for agents that modulate the activity of the RCC356 receptor. The invention also encompasses diagnostic and other assays performed based upon the RCC356/isovaleric acid interaction, as well as kits for performing diagnostic and screening assays.

11 Claims, 9 Drawing Sheets

ATGATGGTGGATCCCAATGGCAATGAATCCAGTGCTACATACTTCATCCTAATAGGCCTCCCTG
GTTTAGAAGAGGCTCAGTTCTGGTTGGCCTTCCCATTGTGCTCCCTCTACCTTATTGCTGTGCTA
GGTAACTTGACAATCATCTACATTGTGCGGACTGAGCACAGCCTGCATGAGCCCATGTATATATT
TCTTTGCATGCTTTCAGGCATTGACATCCTCATCTCCACCTCATCCATGCCCAAAATGCTGGCCA
TCTTCTGGTTCAATTCCACTACCATCCAGTTTGATGCTTGTCTGCTACAGATGTTTGCCATCCAC
TCCTTATCTGGCATGGAATCCACAGTGCTGCTGGCCATGGCTTTTGACCGCTATGTGGCCATCT
GTCACCCACTGCGCCATGCCACAGTACTTACGTTGCCTCGTGTCACCAAAATTGGTGTGGCTGC
TGTGGTGCGGGGGGCTGCACTGATGGCACCCCTTCCTGTCTTCATCAAGCAGCTGCCCTTCTGC
CGCTCCAATATCCTTTCCCATTCCTACTGCCTACACCAAGATGTCATGAAGCTGGCCTGTGATGA
TATCCGGGTCAATGTCGTCTATGGCCTTATCGTCATCATCTCCGCCATTGGCCTGGACTCACTTC
TCATCTCCTTCTCATATCTGCTTATTCTTAAGACTGTGTTGGGCTTGACACGTGAAGCCCAGGCC
AAGGCATTTGGCACTTGCGTCTCTCATGTGTGTGCTGTGTTCATATTCTATGTACCTTTCATTGG
ATTGTCCATGGTGCATCGCTTTAGCAAGCGGCGTGACTCTCCGCTGCCCGTCATCTTGGCCAAT
ATCTATCTGCTGGTTCCTCCTGTGCTCAACCCAATTGTCTATGGAGTGAAGACAAAGGAGATTC
GACAGCGCATCCTTCGACTTTTCCATGTGGCCACACACGCTTCAGAGCCCTAG

MMVDPNGNESSATYFILIGLPGLEEAQFWLAFPLCSLYLIAVLGNLTIIYIVRTEHSLHEPMYIFLCML
SGIDILISTSSMPKMLAIFWFNSTTIQFDACLLQMFAIHSLSGMESTVLLAMAFDRYVAICHPLRHAT
VLTLPRVTKIGVAAVVRGAALMAPLPVFIKQLPFCRSNILSHSYCLHQDVMKLACDDIRVNVVYGLIV
IISAIGLDSLLISFSYLLILKTVLGLTREAQAKAFGTCVSHVCAVFIFYVPFIGLSMVHRFSKRRDSPLP
VILANIYLLVPPVLNPIVYGVKTKEIRQRILRLFHVATHASEP*

Figure 1

| R | COOH | STRUCTURE | CONCENTRATION-RESPONSE CURVE | Log Ec50 |
|---|---|---|---|---|
| HEXAHYDROBENZOIC ACID - CYCLOHEXANE CARBOXYLIC ACID | | | | |
| (CH2)5 - CH | COOH | 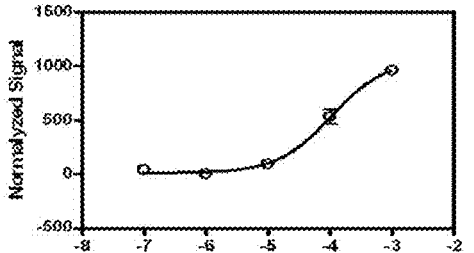 | 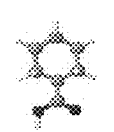 | -3.982 |
| 5-HEXENOIC ACID | | | | |
| CH2-CH-(CH2)3 | COOH | 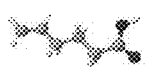 | 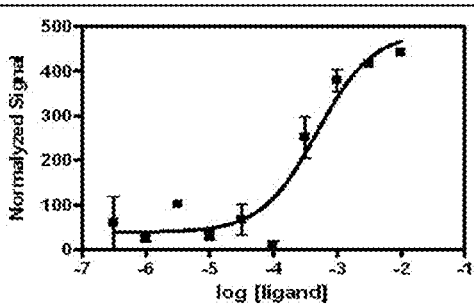 | -3.314 |
Figure 3D A
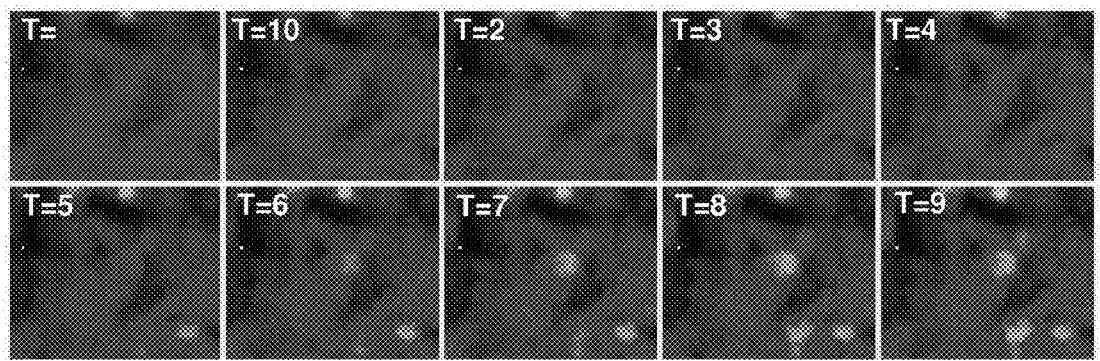
B
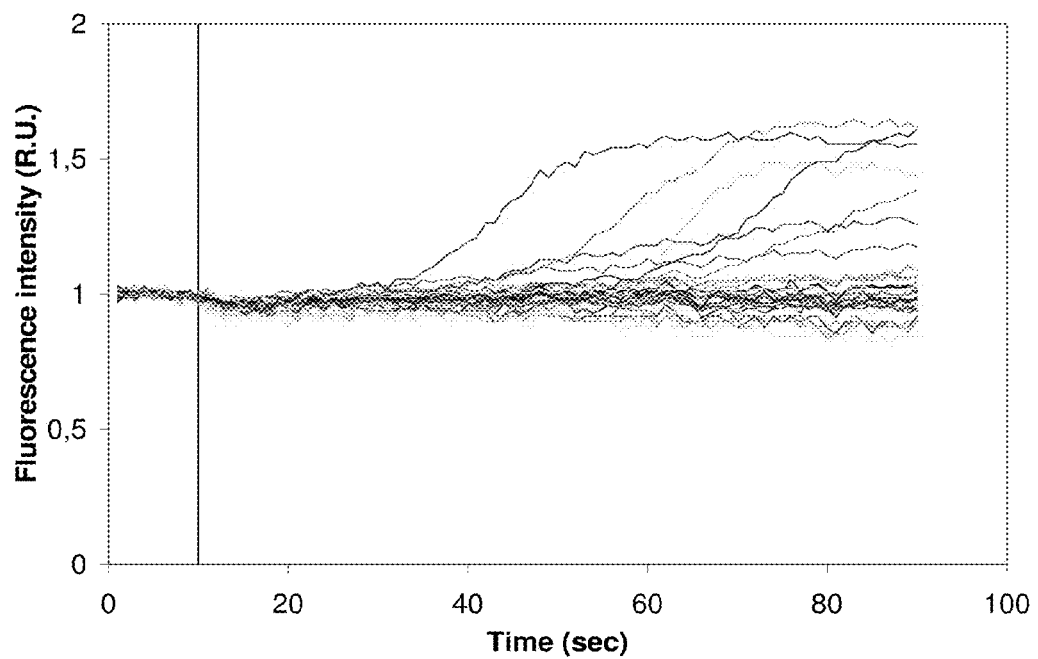
Figure 4

A
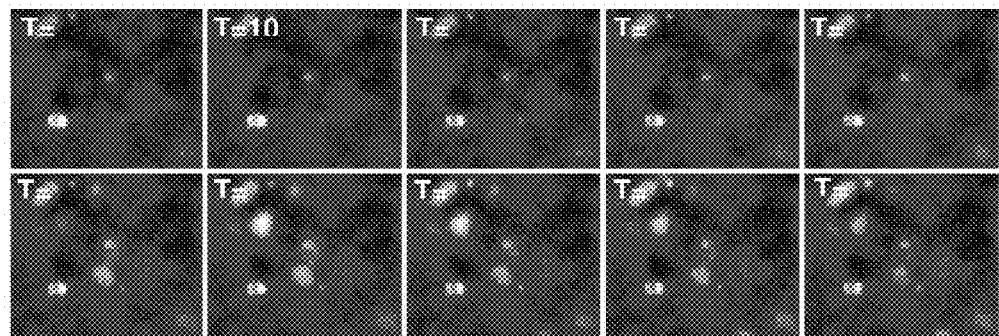
B
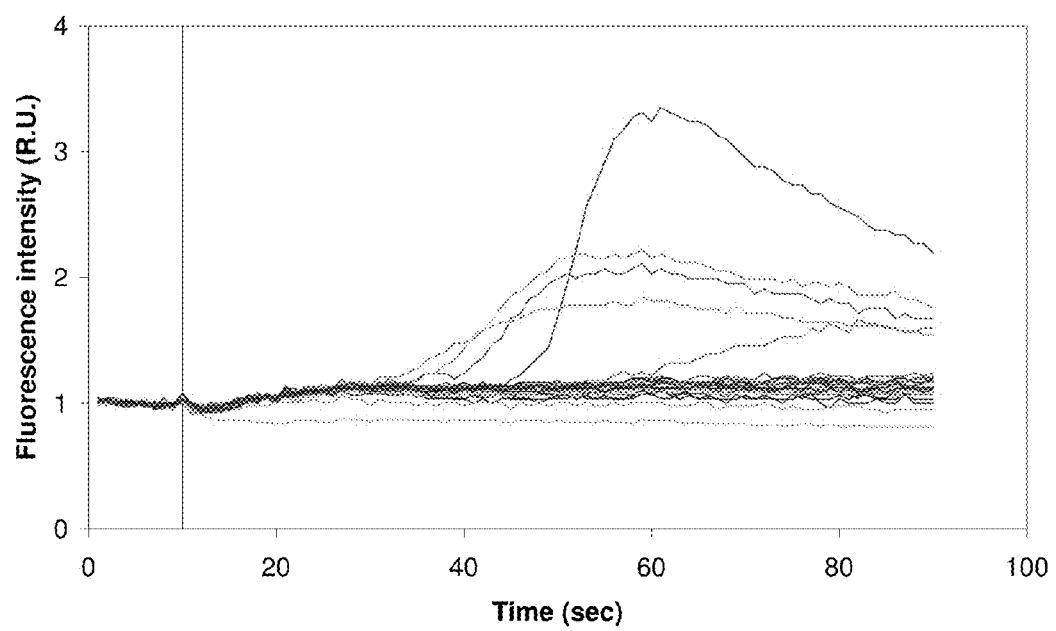
Figure 5

A
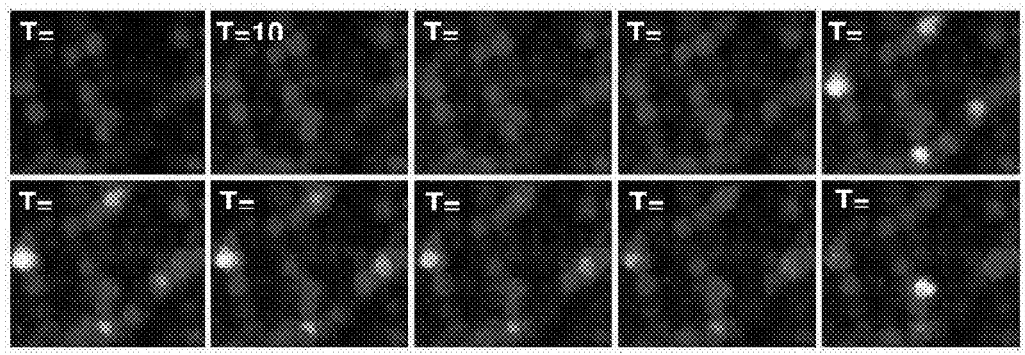
B
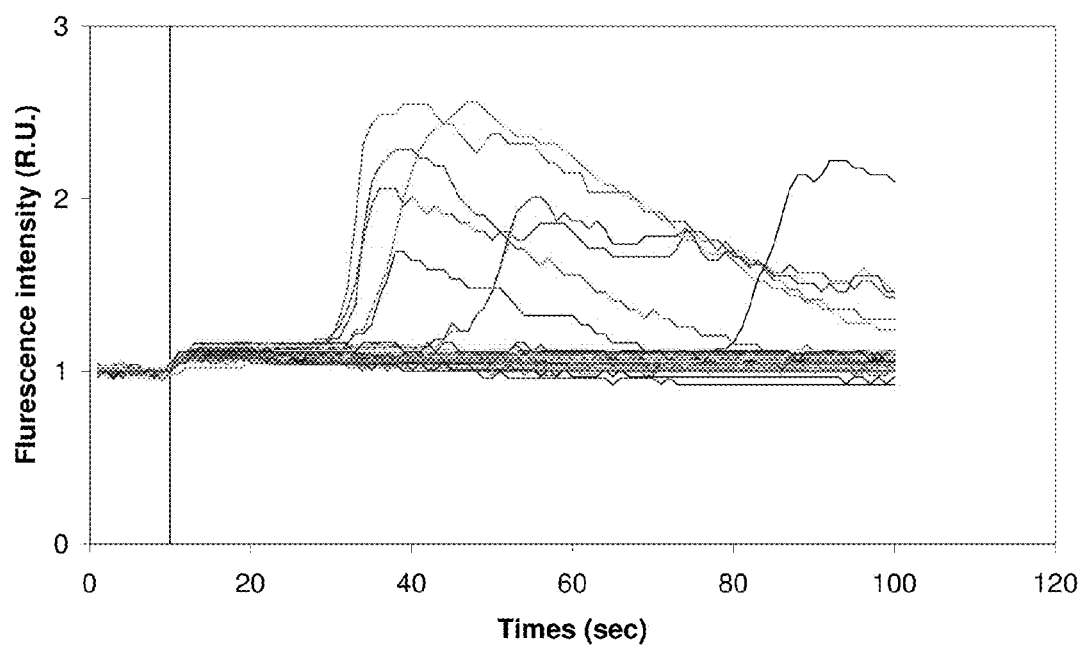
Figure 6

SEQUENCE LISTING

<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Substrate for protein tyrosine kinase

<400> SEQUENCE: 1

Arg Arg Leu Ile Glu Asp Ala Glu Tyr Ala Ala Arg Gly
1               5                   10

```
<210> SEQ ID NO 2
<211> LENGTH: 7
<212> TYPE: PRT
<213> ORGANISM: Artificial Sequence
<220> FEATURE:
<223> OTHER INFORMATION: peptide derived from MARCKS

<400> SEQUENCE: 2

Phe Lys Lys Ser Phe Lys Leu
1               5

<210> SEQ ID NO 3
<211> LENGTH: 11
<212> TYPE: DNA
<213> ORGANISM: Homo sapiens

<400> SEQUENCE: 3
ggggactttc c                                                          11

<210> SEQ ID NO 4
<211> LENGTH: 957
<212> TYPE: DNA
<213> ORGANISM: Homo sapiens

<400> SEQUENCE: 4
atgatggtgg atcccaatgg caatgaatcc agtgctacat acttcatcct aataggcctc     60
cctggtttag aagaggctca gttctggttg gccttcccat tgtgctccct ctaccttatt    120
gctgtgctag gtaacttgac aatcatctac attgtgcgga ctgagcacag cctgcatgag    180
cccatgtata tatttctttg catgctttca ggcattgaca tcctcatctc cacctcatcc    240
atgcccaaaa tgctggccat cttctggttc aattccacta ccatccagtt tgatgcttgt    300
ctgctacaga tgtttgccat ccactcctta tctggcatgg aatccacagt gctgctggcc    360
atggcttttg accgctatgt ggccatctgt cacccactgc gccatgccac agtacttacg    420
ttgcctcgtg tcaccaaaat tggtgtggct gctgtggtgc ggggggctgc actgatggca    480
ccccttcctg tcttcatcaa gcagctgccc ttctgccgct ccaatatcct ttcccattcc    540
tactgcctac accaagatgt catgaagctg gcctgtgatg atatccgggt caatgtcgtc    600
tatggcctta tcgtcatcat ctccgccatt ggcctggact cacttctcat ctccttctca    660
tatctgctta ttcttaagac tgtgttgggc ttgacacgtg aagcccaggc caaggcattt    720
ggcacttgcg tctctcatgt gtgtgctgtg ttcatattct atgtaccttt cattggattg    780
tccatggtgc atcgctttag caagcggcgt gactctccgc tgcccgtcat cttggccaat    840
atctatctgc tggttcctcc tgtgctcaac ccaattgtct atggagtgaa gacaaaggag    900
attcgacagc gcatccttcg acttttccat gtggccacac acgcttcaga gccctag      957

<210> SEQ ID NO 5
<211> LENGTH: 318
<212> TYPE: PRT
<213> ORGANISM: Homo sapiens

<400> SEQUENCE: 5

Met Met Val Asp Pro Asn Gly Asn Glu Ser Ser Ala Thr Tyr Phe Ile
1               5                   10                  15
Leu Ile Gly Leu Pro Gly Leu Glu Glu Ala Gln Phe Trp Leu Ala Phe
            20                  25                  30
Pro Leu Cys Ser Leu Tyr Leu Ile Ala Val Leu Gly Asn Leu Thr Ile
        35                  40                  45
```

-continued

```
Ile Tyr Ile Val Arg Thr Glu His Ser Leu His Glu Pro Met Tyr Ile
 50                      55                  60

Phe Leu Cys Met Leu Ser Gly Ile Asp Ile Leu Ile Ser Thr Ser Ser
 65              70                  75                      80

Met Pro Lys Met Leu Ala Ile Phe Trp Phe Asn Ser Thr Thr Ile Gln
             85                      90                  95

Phe Asp Ala Cys Leu Leu Gln Met Phe Ala Ile His Ser Leu Ser Gly
            100                 105             110

Met Glu Ser Thr Val Leu Leu Ala Met Ala Phe Asp Arg Tyr Val Ala
        115                 120             125

Ile Cys His Pro Leu Arg His Ala Thr Val Leu Thr Leu Pro Arg Val
    130                 135             140

Thr Lys Ile Gly Val Ala Ala Val Val Arg Gly Ala Ala Leu Met Ala
145             150             155                         160

Pro Leu Pro Val Phe Ile Lys Gln Leu Pro Phe Cys Arg Ser Asn Ile
                165                 170             175

Leu Ser His Ser Tyr Cys Leu His Gln Asp Val Met Lys Leu Ala Cys
            180             185                 190

Asp Asp Ile Arg Val Asn Val Val Tyr Gly Leu Ile Val Ile Ile Ser
            195             200             205

Ala Ile Gly Leu Asp Ser Leu Leu Ile Ser Phe Ser Tyr Leu Leu Ile
    210             215             220

Leu Lys Thr Val Leu Gly Leu Thr Arg Glu Ala Gln Ala Lys Ala Phe
225             230             235                         240

Gly Thr Cys Val Ser His Val Cys Ala Val Phe Ile Phe Tyr Val Pro
                245             250             255

Phe Ile Gly Leu Ser Met Val His Arg Phe Ser Lys Arg Arg Asp Ser
                260             265             270

Pro Leu Pro Val Ile Leu Ala Asn Ile Tyr Leu Leu Val Pro Pro Val
            275             280             285

Leu Asn Pro Ile Val Tyr Gly Val Lys Thr Lys Glu Ile Arg Gln Arg
    290             295             300

Ile Leu Arg Leu Phe His Val Ala Thr His Ala Ser Glu Pro
305             310             315
```

NATURAL LIGAND OF G PROTEIN COUPLED RECEPTOR RCC356 AND USES THEREOF

This application is a Continuation of U.S. Application Ser. No. 11/897,793, now abandoned filed on Aug. 30, 2007, which was a Continuation of International Application Ser. No. PCT/EP2006/001904, filed Mar. 2, 2006, which claims priority to EP05447046.3, filed Mar. 3, 2005. The contents of the foregoing are incorporated herein in their entirety.

FIELD OF THE INVENTION

The invention relates to the identification of the natural ligand for the G-Protein Coupled Receptor (GPCR) RCC356 and uses thereof.

BACKGROUND OF THE INVENTION

G-protein coupled receptors (GPCRs) are proteins responsible for transducing a signal within a cell. GPCRs have usually seven transmembrane domains. Upon binding of a ligand to an extra-cellular portion or fragment of a GPCR, a signal is transduced within the cell that results in a change in a biological or physiological property or behaviour of the cell. GPCRs, along with G-proteins and effectors (intracellular enzymes and channels modulated by G-proteins), are the components of a modular signaling system that connects the state of intra-cellular second messengers to extra-cellular inputs.

GPCR genes and gene products can modulate various physiological processes and are potential causative agents of disease. The GPCRs seem to be of critical importance to both the central nervous system and peripheral physiological processes.

The GPCR protein superfamily is represented in five families: Family I, receptors typified by rhodopsin and the beta2-adrenergic receptor and currently represented by over 200 unique members; Family II, the parathyroid hormone/calcitonin/secretin receptor family; Family III, the metabotropic glutamate receptor family, Family IV, the CAMP receptor family, important in the chemotaxis and development of *D. discoideum*; and Family V, the fungal mating pheromone receptor such as STE2.

G proteins represent a family of heterotrimeric proteins composed of α, β and γ subunits, that bind guanine nucleotides. These proteins are usually linked to cell surface receptors (receptors containing seven transmembrane domains) for signal transduction. Indeed, following ligand binding to the GPCR, a conformational change is transmitted to the G protein, which causes the α-subunit to exchange a bound GDP molecule for a GTP molecule and to dissociate from the βγ-subunits.

The GTP-bound form of the α, β and γ-subunits typically functions as an effector-modulating moiety, leading to the production of second messengers, such as cAMP (e.g. by activation of adenyl cyclase), diacylglycerol or inositol phosphates.

Greater than 20 different types of α-subunits are known in humans. These subunits associate with a small pool of β and γ subunits. Examples of mammalian G proteins include Gi, Go, Gq, Gs, G-olf and Gt. G proteins are described extensively in Lodish et al., *Molecular Cell Biology* (Scientific American Books Inc., New York, N.Y., 1995; and also by Downes and Gautam, 1999, The G-Protein Subunit Gene Families. Genomics 62:544-552), the contents of both of which are incorporated herein by reference.

Known and uncharacterized GPCRs currently constitute major targets for drug action and development. For some GPCRs a possible physiological role has been assigned, however no ligands capable of modulating said receptor have been identified yet. There are ongoing efforts to identify new G protein coupled receptors which can be used to screen for new agonists and antagonists having potential prophylactic and therapeutical properties.

More than 300 GPCRs have been cloned to date. Mechanistically, approximately 50-60% of all clinically relevant drugs act by modulating the functions of various GPCRs (Cudermann et al., *J. Mol. Med.*, 73:51-63, 1995).

The sense of smell allows chemical communications between living organisms from invertebrates to mammals and environment. Perception and discrimination of thousands of odorants is made through olfaction. Such chemical signalling may modulate social behaviour of most animal species which rely on odorant compounds to identify kin or mate, to locate food or to recognize territory for instance. Smelling abilities are initially determined by neurons in the olfactory epithelium, the olfactory sensory neurons (OSN). Therein, odorant molecules bind to olfactory receptor proteins (OR), also known as odorant receptors. These OR are members of the G-protein coupled receptors (GPCR) superfamily. They are encoded by the largest gene family. While in rodents as many as 1,300 different OR genes have been identified, around 800 OR genes have been identified in the human genome. Each olfactory neuron is thought to express only one type of OR, forming therefore cellular basis of odorant discrimination by olfactory neurons. They are synthesized in the endoplasmatic reticulum, transported and eventually concentrated at the cell surface membrane of the cilia at the tip of the dendrite. Similarly, ORs are found at the axon terminal of OSN. They are assumed to play a role in targeting axons to OR-specific olfactory bulb areas.

Most mammals have a secondary olfactory system, the vomeronasal system. The vomeronasal organ is localized in nasal cavity and is partly made of vomeronasal sensory neurons. This system would be responsible for detecting pheromones through activation of pheromone receptors. However, there is no evidence to affirm that detection of pheromone is solely done through vomeronasal sensory neurons and that vomeronasal sensory neurons detect pheromone only. Pheromone receptors are also 7TM proteins, but they are completely distinct from the OR superfamily. Even though pheromone receptors are part of the GPCR superfamily, no G-protein coupled to those receptors has been identified yet. Two families of pheromone receptors have been listed to date: the V1R and the V2R families. Receptors of both of them have been identified in mouse (more than 300) while only 5 receptors of the V1R family in human.

Taste is also part of chemosensation. It relies on the activation of taste receptors localized on the tongue and palate in human. They are expressed in taste receptor cells (TCRs) part of taste buds. These cells are specialized epithelium cells that contact neurons, which in turn relay the information to the brain. Thereby, unlike OSN, TCRs are not neuron cells. As olfactory receptors, taste receptors are part of the GPCR superfamily. Today, 2 families have been identified: T1R and T2R families. While human T1R family is made of three receptors namely T1R1, T1R2 and T1R3, T2R family is made of 25 putative receptors in human. T2R receptors are responsible for bitter taste detection and would be functional as monomers. However, T1R receptors are thought to work as dimmers. Dimerization would confer specificity to receptors. Heterodimers of T1R1/T1R3 detect umami taste, while T1R2/T1R3 heterodimers are activated by sweet compounds.

Besides those two families, other proteins are thought to be taste receptors such as TRMP5, a potential channel, mGluR4 that might function as an umami receptor, ASIC2, a sour taste receptor, ENaC, a salt taste receptor, VN1, a burning taste receptor or TMP8, a cold taste receptor.

Smell, taste and pheromones constantly influence personal behaviour of animals and humans. It is thus of great importance to understand mechanisms of said perceptions. Most particularly to determine means to influence it. Already known is that olfactory, taste and pheromone systems do not follow the one ligand/one receptor rules. Several ligands have been described in the literature to activate same receptors. Therefore said sensory systems are probably part of a system wherein different receptors may be activated by same ligands, and wherein one receptor may be modulated by different ligands.

RCC356, also termed PHOR-1, has previously been characterized and described as a novel prostate-specific GPCR upregulated in prostate cancer (U.S. Pat. No. 6,790,631 and US2004/0248088). The human polynucleotide sequence of RCC356 is shown in FIG. 1a; the human amino acid sequence of RCC356 in FIG. 1b. Said amino acid sequence shows one or more GPCR signature sequences and olfactory receptor signatures. RCC356 can thereby be considered as an olfactory receptor (OR). That this OR may have a prostate specific function is not exceptional. Indeed, OR genes were found to be expressed in tissues other than the olfactory epithelium, indicating potential alternative biological roles of this class of chemosensory receptors. In particular, it has been previously shown that ORs, other than RCC356, are also expressed in germ cells, testis, insuline-secreting β-cells, spleen, specific brain areas and heart (Parmentier et al. 1992, Nature, 355: 453-455; Thomas et al. 1996, Gene, 178:1-5; Nef and Nef 1997, Proc., Natl. Acad. Sci. USA, 94: 4766-4771; Blache et al. 1998, Biochem. Biophys. Res. Commun., 142 :669-672; Drutel et al, 1995, Receptors Channels 3:33-40; Ferrand et al. 1999, J. Mol. Cell. Cardiol. 31:1137-1142; Raming et al., 1998, Receptors Channels 6 :141-151). Furthermore, a rat olfactory receptor expressed in brain, known as RA1c (Raming et al., 1998, Receptor Channels 6:141), has a sequence with the highest degree of homology to PHOR-01. PHOR-1 is 59.9% identical to RA1c in 299 residue overlap. The likely human homologue of RA1c, HPRAAJ70, also shows a similar degree of homology to PHOR-01. The HPRAAJ70 protein is reported to be a prostate-specific GPCR (U.S. Pat. No. 5,756,309, WO 96/39435) confirming the finding mentioned in U.S. Pat. No. 6,790,631. U.S. Pat. No. 6,790,631 also mentiones that PHOR-01 is restricted to normal prostate, as well as to cancers of the prostate, kidney, uterus, cervix, stomac, and rectum. PHOR-01 may also be expressed in other cancers. Their role in the regulation of cell proliferation and transformation has also been suggested. For instance and as shown in U.S. Pat. No. 6,790,631, PHOR1 may play a critical role in cell proliferation. In this context, U.S. Pat. No. 6,790, 631 proposes to use PHOR-01 in diagnostic and therapeutic methods and compositions useful in the management of various cancers that express PHOR-01, in particular of prostate cancers. Although a potential physiological role has been assigned to RCC356, reducing the doubling time of cells overexpressing RCC356 (U.S. Pat. No. 6,790,631), there is until now no indication by which ligand said receptor may be modulated.

Isovalaric acid is an unpleasant smelling organic acid forming part of the malodour formation of human and animal secretions, particular of sweat. Another constituent of human sweat is 3-methyl-2-hexenoic acid, of foul malodour is propionic acid, and of pet malodor is hexenoic acid. Said compounds were previously described as being recognized by a subgenus of olfactory receptors (US2003/0207337). Olfactory receptors belong to the 7-transmembrane receptor superfamily (Buck et al., Cell 65:175-87, 1991) which is known as G-protein coupled receptors (GPCRs). GPCRs mediate transmembrane signalling which controls many physiological functions, such as endocrine function, exocrine function, heart rate, lipolysis, carbohydrate metabolism, neurotransmission, vision, and taste reception. The olfactory receptors specifically recognize molecules that elicit specific olfactory sensation. These molecules are also referred to as 'odorants'. Genes coding for the olfactory receptors are active primarily in olfactory neurons (Axel, Sci. Amer. 273:154-59, 1995). Individual olfactory receptor subtypes are expressed in subsets of cells distributed in distinct zones of the olfactory epithelium (Breer, Semin. Cell Biol., 5:25-32, 1994). But, as mentioned above, expression of OR is not limited to olfactory epithelium. Many laboratories have evidenced expression of OR in other tissues including prostate, brain, lung, liver, kidney, cervix, and breast.

SUMMARY OF THE INVENTION

The present invention relates to the identification of isovaleric acid (IVA) as a natural ligand of the RCC356 GPCR (G-protein coupled receptor). The invention encompasses the use of the interaction of RCC356 polypeptides and isovaleric acid as the basis of screening assays for agents that modulate the activity of the RCC356 receptor.

The invention also encompasses diagnostic and other methods based upon the RCC356/isovaleric acid interaction, as well as kits for performing diagnostic and screening methods. In particular, the present invention indicates that isovaleric acid has a link towards cancer progression and/or development. In addition, the present invention suggests that RCC356 may play a role in odor recognition and neurological activities.

The invention encompasses a method of identifying an agent that binds to RCC356, said method comprising: a) contacting a RCC356 polypeptide with isovaleric acid in the presence or in the absence of a candidate modulator under conditions permitting the binding of said isovaleric acid to said RCC356 polypeptide; and b) measuring the binding of said RCC356 polypeptide to said isovaleric acid, wherein a decrease in binding in the presence of said candidate modulator, relative to the binding in the absence of the candidate modulator, identifies the candidate modulator as an agent that modulates the function of RCC356.

The invention further encompasses a method of detecting in a sample the presence of an agent that binds to RCC356 in a sample, said method comprising a) contacting a RCC356 polypeptide with isovaleric acid in the presence or in the absence of said sample under conditions permitting the binding of said isovaleric acid to said RCC356 polypeptide; and b) measuring the binding of said RCC356 polypeptide to said isovaleric acid, wherein a decrease in binding in the presence of the sample, relative to the binding in the absence of the candidate modulator, indicates the presence, in the sample of an agent that modulates the function of RCC356 in said sample.

The invention further encompasses a method of identifying an agent that modulates the function of RCC356, said method comprising: a) contacting a RCC356 polypeptide with isovaleric acid in the presence or in the absence of a candidate modulator, under conditions permitting activation of said RCC356 polypeptide by isovaleric acid; and b) measuring a signaling activity of said RCC356 polypeptide, wherein a change in the activity in the presence of said candidate modulator relative to the activity in the absence of said candidate modulator identifies said candidate modulator as an agent that modulates the function of RCC356.

The invention further encompasses a method of identifying an agent that modulates the function of RCC356, said method comprising: a) contacting a RCC356 polypeptide with a candidate modulator; b) measuring a signaling activity of said RCC356 polypeptide in the presence of said candidate modulator; and c) comparing the activity measured in the presence of said candidate modulator to said activity measured in a sample in which said RCC356 polypeptide is contacted with isovaleric acid at its $EC_{50}$, wherein said candidate modulator is identified as an agent that modulates the function of RCC356 when the amount of the activity measured in the presence of the candidate modulator is at least 10% of the amount induced by said isovaleric acid present at its $EC_{50}$. According to the invention, the amount of the activity measured in the presence of the candidate modulator may be 15%, 20%, 25%, 30%, 35%, 40%, 45%, 50%, 55%, 60%, 65%, 70%, 75%, 80%, 85%, 90%, 95%, 100% or even higher of the amount induced by isovaleric acid present at its $EC_{50}$. The present invention further indicates that, when applicable, in the methods of the present invention, isovaleric acid present at its $EC_{50}$ is preferably used. However, in the methods of the present invention, isovaleric acid may be applied at other concentrations at which activation of RCC356 may be detected.

The invention further encompasses a method of detecting in a sample the presence of an agent that modulates the function of RCC356, said method comprising: a) contacting a RCC356 polypeptide with isovaleric acid in the presence or in the absence of said sample; b) measuring a signaling activity of said RCC356 polypeptide; and c) comparing the amount of said activity measured in a reaction containing RCC356 and isovaleric acid without said sample to the amount of said activity measured in a reaction containing RCC356, isovaleric acid and said sample, wherein a change in said activity in the presence of said sample relative to the activity in the absence of said sample indicates the presence of an agent that modulates the function of RCC356 in said sample.

The invention further encompasses a method of detecting in a sample the presence of an agent that modulates the function of RCC356, said method comprising: a) contacting a RCC356 polypeptide with said sample; b) measuring a signaling activity of said RCC356 polypeptide in the presence of said sample; and c) comparing said activity measured in the presence of said sample to said activity measured in a reaction in which said RCC356 polypeptide is contacted with isovaleric acid present at its $EC_{50}$, wherein an agent that modulates the function of RCC356 is detected if the amount of the activity measured in the presence of said sample is at least 10% of the amount induced by isovaleric acid present at its $EC_{50}$.

According to the present invention, when using binding methods isovaleric acid may be detectably labeled. In said methods, isovaleric acid may be detectably labeled with a moiety selected from the group consisting of a radioisotope, a fluorophore, and a quencher of fluorescence. Alternatively, isovaleric acid may be detectably labelled with an NMR-detectable moiety.

In one embodiment of any of the preceding methods, the contacting is performed in or on a cell expressing said RCC356 polypeptide. According to the present invention, said cell may be, but is not limited to, Human embryonic kidney cells (Hek293), Chinese hamster cells (CHO), Monkey cells (COS), primary olfactory cells, *Xenopus* cells, insect cells, yeast or bacteria.

In another embodiment of any of the preceding methods, the contacting is performed in or on synthetic liposomes (see Tajib et al., 2000, *Nature Biotechnology* 18: 649-654, which is incorporated herein by reference) or virus-induced budding membranes containing a RCC356 polypeptide (see WO0102551, 2001, incorporated herein by reference).

In another embodiment of any of the preceding methods, the method is performed using a membrane fraction from cells expressing said RCC356 polypeptide.

In a preferred embodiment of either of the preceding methods, the method is performed on a protein chip.

In another preferred embodiment of either of the preceding methods, the measuring is performed using a method selected from label displacement, surface plasmon resonance, fluorescence resonance energy transfer, fluorescence quenching, and fluorescence polarization.

In another embodiment of either of the preceding methods, the agent is selected from the group consisting of a peptide, a polypeptide, an antibody or antigen-binding fragment thereof, a lipid, a carbohydrate, a nucleic acid, and a small organic molecule including but not limited to an odorant compound and a pheromone.

According to the present invention, when a functional assay is used, the step of measuring a signaling activity of the RCC356 polypeptide may comprise detecting a change in the level of a second messenger.

In another embodiment, the step of measuring a signaling activity comprises measurement of guanine nucleotide binding/coupling or exchange, adenylate cyclase activity, cAMP, Protein Kinase C activity, Protein Kinase A activity phosphatidylinositol breakdown, diacylglycerol, inositol triphosphate, intracellular calcium, calcium flux, arachinoid acid, MAP kinase activity, tyrosine kinase activity, melanophore assay, receptor initialization assay, or reporter gene expression. When the G-protein binding/coupling or exchange is measured, of all Gα subunits possible preferably the behavious of GTP-binding protein G protein alpha-olf subunit (olfactory), also G-olf, is studied. The sequence of the human G-olf subunit has been deposited previously at the Genebank under accession number L10665. However, G-olf subunits of other species may be used and studied.

In a preferred embodiment, the measuring of the signaling activity comprises using a fluorescence or luminescence assay. Fluorescence and luminescence assays may comprise the use of Ca2+ sensitive fluorophores including fluo3, Fluo4 or Fura, (Molecular probes); Ca3-kit family (Molecular Device) and aequorin. Furthermore, said assays may apply an automated fluorometric or luminescent reader such as FDSS (Hammamatsu) or FLIPR (Molecular Device).

The invention further encompasses a method of modulating the activity of a RCC356 polypeptide in a cell, said method comprising the step of delivering to said cell isovaleric acid that modulates the activity of a RCC356 polypeptide, such that the activity of RCC356 is modulated.

In another embodiment of any of the preceding methods, the method is a high throughput screening method.

In another embodiment of any of the preceding methods, the agent is part of a chemical library or animal organ extracts. Said animal organ extracts may be, but are not limited to, extracts prepared from prostate cancer, blood serum, brain.

The invention further encompasses an isovaleric acid-related agent identified or detected by any of the preceeding methods. Said isovaleric acid-related agent may be an agonist, an antagonist, or an inverse agonist for RCC356.

The invention also encompasses a composition comprising an isovaleric acid-related agent identified or detected by any of the preceeding methods.

According to the present invention, the agent identified or detected by any of the preceeding methods, or the composition comprising said agent, may be used for the preparation of a medicament. Alternatively, these may be used for the preparation of odorants or odorant antagonists. For instance a RCC356 agonist may be used as repellant, a RCC356 antagonist as deodorant.

In a preferred embodiment, the above-mentioned agent or composition may be used for the preparation of a medicament for the treatment of a RCC356-related disease or a RCC356-related disorder; wherein said disease or disorder is preferentially chosen from the group consisting of Cancer and Tumor metastasis. According to the present invention, said disease or disorder may be chosen from the group consisting of prostate-, cervix-, uterus-, rectum-, stomach- and kidney-cancer.

In another preferred embodiment, said an agent or composition may be used for the preparation of a medicament for the treatment of a RCC356-related disease or a RCC356-related disorder; wherein said disease or disorder is preferentially a CNS disorder or disease. According to the present invention, said CNS disease or disorder may be epilepsy.

The present invention also encompasses a composition comprising an isolated RCC356 polypeptide and isovaleric acid.

The present invention also relates to the use of isovaleric acid for the production of a composition comprising an isolated RCC356 polypeptide and said acid.

The present invention further relates to the use of isovaleric acid for the production of a kit for screening agents that modulate the signaling of RCC356, for the production of a kit for the diagnosis or prognosis of a disease characterized by the dysregulation of RCC356 signaling, or in combination with RCC356 for the production of a kit to screen odorants or odorant antagonists.

In addition, the present invention encompasses the use of isovaleric acid as ligand for RCC356.

The present invention further encompasses the use of isovaleric acid for the preparation of a medicament. According to the present invention, said medicament may be used for the treatment of a RCC356-related disease or a RCC356-related disorder; wherein said disease or disorder is preferentially chosen from the group consisting of Cancer and Tumor metastasis. In particular, said medicament may be used for the treatment of prostate-, cervix-, uterus-, rectum-, stomach- and/or kidney-cancer.

Alternatively, said medicament may be used for the treatment of a RCC356-related disease or a RCC356-related disorder; wherein said disease or disorder is preferentially a CNS disorder or disease. In particular, said medicament may be used for the treatment of epilepsy.

The present invention also relates to an antibody recognizing the IVA/RCC356 complex or fragments thereof.

Another embodiment of the invention relates to the use of RCC356 fragments or antibodies recognizing RCC356 or antibodies recognizing the IVA/RCC356 complex, for the preparation of a medicament for the treatment of a CNS disorder or disease. Said CNS disease or disorder may be epilepsy.

Another embodiment of the invention relates to the use of RCC356 fragments, antibodies recognizing RCC356 or antibodies recognizing IVA/RCC356 complex, for the preparation of a medicament for the treatment of (isovaleric acid-related) olfactory malfunction.

Alternatively, antibodies recognizing the IVA/RCC356 complex may be used for the preparation of a medicament for the treatment of cancer or tumor metastatis.

The invention further encompasses a method of diagnosing or prognosing a disease or disorder characterized by dysregulation of RCC356 signaling, said method comprising: a) contacting a tissue sample with isovaleric acid; b) detecting binding of said acid to said tissue sample; and c) comparing the binding detected in step (b) with a standard, wherein a difference in binding relative to said standard is diagnostic or prognostic of a disease or disorder characterized by dysregulation of RCC356.

The invention further encompasses a method of diagnosing or prognosing a disease or disorder characterized by dysregulation of RCC356 signaling, said method comprising: a) contacting a tissue sample with an antibody specific for isovaleric acid or an antibody specific for the IVA/RCC356 complex; b) detecting binding of said antibody to said tissue sample; and c) comparing the binding detected in step (b) with a standard, wherein a difference in binding relative to the standard is diagnostic or prognostic of a disease or disorder characterized by dysregulation of RCC356.

The invention further encompasses a method of diagnosing or prognosing a disease or disorder characterized by dysregulation of RCC356 signaling, said method comprising: a) contacting a tissue sample with an antibody specific for RCC356 and an antibody specific for isovaleric acid or an antibody specific for the IVA/RCC356 complex; b) detecting binding of said antibodies to said tissue sample; and c) comparing the binding detected in step (b) with a standard, wherein a difference in binding of either antibody or both, relative to said standard, is diagnostic or prognostic of a disease or disorder characterized by dysregulation of RCC356.

The invention further encompasses a method of diagnosing or prognosing a disease or disorder characterized by dysregulation of RCC356 signaling, said method comprising: a) quantifying the content of isovaleric acid of a tissue sample; and, b) comparing the amount of said acid quantified in step (a) with a standard, wherein a difference in said amount of isovaleric acid relative to said standard is diagnostic or prognostic of a disease or disorder characterized by dysregulation of RCC356.

The RCC356-related disease or the RCC356-related disorder diagnosed or prognosed using a method according to the present invention may be chosen from the group consisting of but not limited to Cancer and Tumor metastasis. In particular, said disease or disorder may be chosen from the group consisting of but not limited to prostate-, cervix-, uterus-, rectum-, stomach- and kidney-cancer.

Alternatively, the RCC356-related disease or the RCC356-related disorder diagnosed or prognosed using a method according to the present invention may be a CNS disorder or disease. For instance, said CNS disease or disorder may be epilepsy.

The present invention further indicates that the antibody specific for the IVA/RCC356 complex may be used to diagnose or prognose a CNS disease or disorder or an isovaleric acid related) olfactory malfunctioning. As indicated above, said CNS disease or disorder may be epilepsy.

The present invention also encompasses a method of diagnosing or prognosing (isovaleric acid-related) olfactory malfunctioning or a CNS-related disorder or disease, said method comprising: a) quantifying the content of RCC356 of a tissue sample; and b) comparing the amount of said receptor quantified in step (a) with a standard, wherein a difference in said amount of RCC356 relative to said standard is diagnostic or prognostic of olfactory malfunctioning or diagnostic or prognostic of CNS-related disorder or disease. According to the present invention, said CNS-related disease or disorder may be epilepsy. In said method the quantification may be performed using RCC356 antibodies, IVA/RCC356 antibodies or isovaleric acid.

The present invention further encompasses a method of diagnosing or prognosing (isovaleric acid-related) olfactory malfunctioning or a CNS-related disorder or disease, said method comprising: a) quantifying the mRNA encoding RCC356 and/or verifying the correctness of the RCC356 sequence compared to the wild type RCC356 sequence in a tissue sample; and b) comparing the amount and/or the correctness of said nucleic acid quantified or determined in step (a) with a standard, wherein a difference in said amount or a difference in sequence of RCC356 relative to said standard is diagnostic or prognostic of (isovaleric acid-related) olfactory malfunctioning or diagnostic or prognostic of CNS-related disorder or disease. In said method, said CNS-related disease or disorder may be epilepsy.

The present invention also encompasses a method of diagnosing or prognosing cancer or tumor metastasis, said method comprising: a) quantifying the content of RCC356 of a tissue sample using IVA/RCC356 antibodies; and b) comparing the amount of said receptor in step a) with a standard, wherein a difference in said amount of RCC356 relative to said standard is diagnostic or prognostic of olfactory malfunctioning or diagnostic or prognostic of cancer or tumor metastasis.

The invention further encompasses a kit comprising an isolated RCC356 polypeptide, isovaleric acid and packaging materials therefor; an isolated polynucleotide encoding a RCC356 polypeptide, isovaleric acid, and packaging materials therefore; a kit comprising a cell expressing a RCC356 polypeptide or membranes thereof, isovaleric acid and packaging materials therefor. Said cell may be transformed with a polynucleotide encoding said RCC356.

According to the present invention, the above-mentioned kits may be used for several purposes. For instance, said kit may be used for screening agents that modulate the signalling of RCC356, for screening odorants or anti-odorant agents, or for screening anticancer compounds or compounds to treat a CNS disorder or disease. When looking for anticancer compounds, the treatment of prostate-, cervix-, uterus-, rectum-, stomach- and kidney-cancer is most particularly aimed at; when looking for compounds to treat CNS disorders, the treatments of especially epilepsy is most particularly aimed at.

In addition, the present invention also relates to the use of a kit comprising isovaleric acid for the diagnosis or prognosis of a disease or disorder characterized by dysregulation of RCC356 signaling.

Furthermore, the present invention relates to the use of a kit comprising an isovaleric acid antibody for the diagnosis or prognosis of a disease or disorder characterized by the dysregulation of RCC356 signalling. According to the present invention, said disease or disorder may be cancer.

The present invention further encompasses the use of a kit comprising RCC356, for the diagnosis or prognosis of CNS-related disease. Said kit may also be used for the diagnosis or prognosis of (isovaleric acid-related) olfactory malfunction.

The present invention also encompasses the use of a transgenic animal for RCC356 or an ortholog thereof to study the effect of isovaleric acid on cancer progression and/or treatment. The cancer for which progression and/or treatment is studied, may be prostate, cervix, uterus, rectum, stomach and kidney cancer. With the term ortholog is meant a gene with similar function to RCC356 in an evolutionary related species.

The present invention also encompasses the use of a transgenic animal for RCC356 or an ortholog thereof to study the progression of CNS disorders or diseases and/or treatment or (isovaleric-acid related) olfactory malfunction. The CNS disorders or diseases for which progression and/or treatment is studied, may be epilepsy.

According to the present invention, a transgenic animal overproducing isovaleric acid may be used to study the progression of cancer and/or treatment. Overproduction in an animal may be induced through for instance the inhibition of IVA degradation.

Alternatively, an RCC356 knock-out transgenic (non-human) animal may be used to study the effect of RCC356 on the progression of (isovaleric acid-related) olfactory malfunction. In addition, an RCC356 knock-out transgenic animal may be used to study the effect of RCC356 on the progression of CNS disorders or diseases. In the present description, RCC356 may be understood as ortholog of RCC356 according to the animal model chosen.

In all the above mentioned methods, agents, uses, compositions or kits of the present invention an equivalent of isovaleric acid or an antibody to said equivalent compound may be used, referred at, applied, or incorporated which binds specifically to and activates a signaling activity of a RCC356 polypeptide represented in FIG. 1b. Said equivalent of isovaleric acid may be chosen from the group consisting of propionic acid, butyric acid, isobutyric acid, valeric acid, hexanoic acid, isohexanoic acids, heptanoic acid, isoheptanoic acids, octanoic acid, isooctanoic acids, nonanoic acid, isononanoic acids, valproic acid, isovaleramide, caproic acid, oenanthylic acid, caprylic acid, hexahydrobenzoic acid, pelargonic acid and 5-hexenoic acid. In particular, said equivalent may be chosen from the group consisting of butyric acid, valeric acid, caproic acid, oenanthylic acid, caprylic acid, hexahydrobenzoic acid, pelargonic acid and 5-hexenoic acid.

In addition, in all the above mentioned methods, uses, compositions or kits of the present invention, the RCC356 polypeptide may have at least 20% identity or higher identity, such as 25, 30, 35, 40, 45, 50, 55, 60, 65, 70, 75, 80, 85, 90, 95 or even 100% to the polypeptide represented in FIG. 1b but with comparable activity to said RCC356 polypeptide. A skilled person knows how to evaluate said activity depending on the assay used.

In addition, in all the above mentioned methods, uses, compositions or kits of the present invention, the RCC356 polypeptide may be a chimera or an active fragment thereof.

As used herein, the term "RCC356 polypeptide" refers to a polypeptide having two essential properties: 1) a RCC356 polypeptide has at least 20% amino acid identity, and preferably 80%, 90%, 95% or higher, including 100% amino acid identity, to the sequence represented in FIG. 1b; and 2) a RCC356 polypeptide has RCC356 activity, i.e., the polypeptide binds isovaleric acid or an equivalent thereof. Said homology may relate to the whole polypeptide or only part of the polypeptide such as CDR domain (ligand-binding domain of the receptor). According to Pilpel and Lancet (Protein Science 8:969-977, 1999) the CDR domain of a GPCR may be defined following the indications published: TM3-#4, TM3-#8, TM3-#11, TM3-#12, TM3-#15, TM4-#11, TM4-#15, TM4-#19, TM4-#22, TM4-#23, TM4-#26, TM5-#3, TM5-#6, TM5-#7, TM5-#10, TM5-#11 and TM5-13, wherein TMx indicates the transmembrane region of said receptor, and # indicates the amino acid position within said region. Optimally, a "RCC356 polypeptide" also has RCC356 signaling activity as defined herein. However, identification of CDR of 7TM receptors is very hazardous and depends of the algorithm applied to define TM. Moreover, according to Pilpel and Lancet, RCC356 would have only 4 TM . As mentioned above said RCC356 polypeptide also includes RCC356 orthologs.

As used herein, the term "RCC356 polynucleotide" refers to a polynucleotide that encodes a RCC356 polypeptide as defined herein.

As used herein, the term "RCC356 activity" refers to specific binding of isovaleric acid or an equivalent thereof by a RCC356 polypeptide.

As used herein, the term "RCC356 signaling activity" refers to the initiation or propagation of signaling by a RCC356 polypeptide. RCC356 signaling activity is monitored by measuring a detectable step in a signaling cascade by assaying one or more of the following: stimulation of GDP for GTP exchange on a G protein and most particularly G-olf; alteration of adenylate cyclase activity; protein kinase C modulation; protein kinase A modulation; phosphatidylinositol breakdown (generating second messengers diacylglycerol, and inositol triphosphate); intracellular calcium flux; activation of MAP kinases; modulation of tyrosine kinases; internalization assay; modulation of gene or reporter gene activity; or melanophore assay. A detectable step in a signaling cascade is considered initiated or mediated if the measurable activity is altered by 10% or more above or below a baseline established in the substantial absence of isovaleric acid relative to any of the RCC356 activity assays described herein below. The measurable activity can be measured directly, as in, for example, measurement of cAMP or diacylglycerol levels. Alternatively, the measurable activity can be measured indirectly, as in, for example, a reporter gene assay. For most of these assays kits are available in the market.

As used herein, the term "detectable step" refers to a step that can be measured, either directly, e.g., by measurement of a second messenger or detection of a modified (e.g., phosphorylated) protein, or indirectly, e.g., by monitoring a downstream effect of that step. For example, adenylate cyclase activation results in the generation of CAMP. The activity of adenylate cyclase can be measured directly, e.g., by an assay that monitors the production of cAMP in the assay, or indirectly, by measurement of actual levels of cAMP and/or calcium flux.

As used herein, the term "isolated" refers to a population of molecules, e.g., polypeptides or polynucleotides, the composition of which is less than 50% (by weight), preferably less than 40% and most preferably 2% or less, contaminating molecules of an unlike nature. When the term "isolated" is applied to a RCC356 polypeptide, it is specifically meant to encompass a RCC356 polypeptide that is associated with or embedded in a lipid membrane.

As used herein, the term "isovaleric acid" refers to a chemical molecule known by a skilled chemist. Alternatively, isovaleric acid also refer to equivalent molecules such as, but not limited by, propionic acid, butyric acid, valeric acid, caproic acid, oenanthylic acid, caprylic acid, pelargonic acid, isocaproic acid, isooenanthylic acid, isocaprylic acid, isopelargonic acid, hexahydrobenzoic acid, 5-hexenoic acid, valproic acid, isovaleramide or a derivative thereof. All said acids may specifically bind and activate a signaling activity of a RCC356 polypeptide. The term "specifically binds" means that isovaleric acid has an $EC_{50}$, $IC_{50}$, or a $K_d$ of 1 mM or less. Derivatives may be similar chemical compounds carrying in at least one position a difference compared to the compound from which it is derived. A general formula for such "isovaleric equivalent" may be $(CH3)_x-(CH2)_y-(CH)_z-COOH$. In addition, different radicals containing different chemical function including but not limited to amine, ketone, ester, ether and alcohol may be grafted to said general formula.

As used herein, the terms "candidate compound" and "candidate modulator" refer to a composition being evaluated for the ability to modulate ligand binding to a RCC356 polypeptide or the ability to modulate an activity of a RCC356 polypeptide. Candidate modulators can be natural or synthetic compounds, including, for example, small molecules, compounds contained in extracts of animal, plant, bacterial or fungal cells, as well as conditioned medium from such cells.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises carbon.

As used herein, the term "change in binding" or "change in activity" and the equivalent terms "difference in binding" or "difference in activity" refer to an at least 10% increase or decrease in binding, or signaling activity in a given assay.

As used herein, the term "conditions permitting the binding of isovaleric acid to RCC356" refers to conditions of, for example, temperature, salt concentration, pH and protein concentration under which isovaleric acid binds RCC356. Exact binding conditions will vary depending upon the nature of the assay, for example, whether the assay uses viable cells or only membrane fraction of cells. However, because RCC356 is a cell surface protein, and because isovaleric acid normally interacts with RCC356 on the cell surface, favored conditions will generally include physiological salt (90 mM) and pH (about 7.0 to 8.0). Temperatures for binding can vary from 4° C. to 37° C., but will preferably be between room temperature and about 37° C. The concentration of isovaleric acid and RCC356 polypeptide in a binding reaction will also vary, but will preferably be about 10 μM (e.g., in a reaction with radiolabeled tracer isovaleric acid, where the concentration is generally below the $K_d$) to 1 mM (e.g., isovaleric acid as competitor). As an example, for a binding assay using RCC356-expressing cells and purified, labeled isovaleric acid, binding is performed using 10 μM labeled isovaleric acid, 1 mM cold isovaleric acid, and 25,000 cells at 27° C. in 250 μl of a binding buffer consisting of 50 mM HEPES (pH 7.4), 1 mM $CaCl_2$, and 0.5% Fatty acid free BSA.

As used herein, the term "sample" refers to the source of molecules being tested for the presence of an agent that modulates binding to or signaling activity of a RCC356 polypeptide. A sample can be an environmental sample, a natural extract of animal, plant yeast or bacterial cells or tissues, a clinical sample, a synthetic sample, or a conditioned medium from recombinant cells or a fermentation process. A "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a RCC356 polypeptide. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the term "decrease in binding" refers to a decrease of at least 10% in the binding of isovaleric acid or other agonist to a RCC356 polypeptide as measured in a binding assay as described herein.

As used herein, the term "second messenger" refers to a molecule, generated or caused to vary in concentration by the activation of a G-Protein Coupled Receptor that participates in the transduction of a signal from that GPCR. Non-limiting examples of second messengers include cAMP, diacylglycerol, inositol triphosphates and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a ligand (e.g., isovaleric acid) with a receptor (e.g., RCC356). As the term is used herein, binding is "specific" if it occurs with an $EC_{50}$ or a $K_d$ of 100 nM or less, generally in the range of 100 μM to 1000 μM. Using odorant functional assay Ec50 found are usually around 10, 100 and even 1 mM, said signals may be considered specific (see FIG. 3). Odorant binding may be considered specific if the $EC_{50}$ or $K_d$ is 1000 μM, 950 μM, 900 μM, 850 μM, 800 μM, 750μ, 700 μM, 650 μM, 600 μM, 550 μM, 500 μM, 450 μM, 400 μM, 350 μM, 300 μM, 250 μM, 200 μM, 150 μM, 100 μM, 75 μM, 50 μM, 25 μM or 10 μM, 1 μM, 950 nM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 75 nM, 50 nM, 25 nM or 10 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 150 pM, 100 pM, 75 pM, 50 pM, 25 pM or 10 pM or less.

As used herein, the term "$EC_{50}$," refers to that concentration of an agent at which a given activity, including binding of isovaleric acid or other ligand and a functional activity of a RCC356 polypeptide, is 50% of the maximum for that RCC356 activity measurable using the same assay. Stated differently, the "$EC_{50}$" is the concentration of agent that gives 50% activation, when 100% activation is set at the amount of activity that does not increase with the addition of more agonist. It should be noted that the "$EC_{50}$ of an isovaleric acid equivalent" will vary with the identity of acid; for example, equivalent isovaleric acid molecules can have $EC_{50}$ values higher than, lower than or the same as isovaleric acid. Therefore, where an equivalent of isovaleric acid is used, one of the skill in the art can determine the $EC_{50}$ for that equivalent according to conventional methods. The $EC_{50}$ of a given isovaleric acid equivalent is measured by performing an assay for an activity of a fixed amount of RCC356 polypeptide in the presence of doses of the isovaleric acid equivalent that increase at least until the RCC356 response is saturated or maximal, and then plotting the measured RCC356 activity versus the concentration of the acid used.

As used herein, the term "Kd" is a dissociation constant or the ligand concentration at which half of the receptors are bound by the ligand at equilibrium.

As used herein, the term "$IC_{50}$" is the concentration of an antagonist or inverse agonist that reduces the maximal activation of a RCC356 receptor by 50%.

As used herein, the term "detectably labeled" refers to the property of a molecule, e.g., a isovaleric acid or an equivalent therefrom, that has a structural modification. Said modification is introduced through the incorporation or addition of a functional group. Said functional group (label) can be readily detected. Detectable labels include but are not limited to fluorescent compounds, isotopic compounds, chemiluminescent compounds, quantum dot labels. Examples of radioisotopes which can be added to the structure of isovaleric acid, or equivalents, may be $^{125}I$, $^{35}S$, $^{14}C$, or $^3H$. Examples of radioisotopes which can be incorporated to the structure of isovaleric acid, or equivalents, may be $^3H$ or $^{14}C$. The various means of detection include but are not limited to spectroscopic, photochemical, radiochemical, biochemical, immunochemical, or chemical means.

As used herein, the term "affinity tag" refers to a label, attached to a molecule of interest (e.g., a RCC356 polypeptide), that confers upon the labeled molecule the ability to be specifically bound by a reagent that binds the label. Affinity tags include, but are not limited to an epitope for an antibody (known as "epitope tags"), biotin, 6×His, Myc, FLAG and GST. Affinity tags can be used for the detection, as well as for the purification of the labeled species.

As used herein, the term "decrease in binding" refers to a decrease of at least 10% in the amount of binding detected in a given assay with a known or suspected modulator of RCC356 relative to binding detected in an assay lacking that known or suspected modulator.

As used herein, the term "delivering," when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. RCC356 is a GPCR.

As used herein, the term "olfactory receptor" is a GPCR with OR signature as defined in Zozulya et al, Genome Biology 2001 2(6) research0018.1-0018.12. Said reference is incorporated herein by reference.

As used herein, the term "agent that modulates the function of a RCC356 polypeptide" is a molecule or compound that increases or decreases RCC356 activity, including compounds that change the binding of isovaleric acid or equivalents thereof, and change RCC356 downstream signaling activities.

As used herein, the term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for a polypeptide conferred by at least one CDR region of the antibody. In preferred embodiments, the antibodies, the antibody further comprises a label attached thereto and able to be detected, (e.g., the label can be a radioisotope, fluorescent compound, chemiluminescent compound, enzyme, or enzyme co-factor).

As used herein, the term "anticancer compound" refers to any compound that stops or inhibits cancer development or progression. As mentioned above, the cancer which may be treated with said anticancer compound may be any cancer or tumor metastasis. Furthermore, said compound may work on the inhibition or arrest of cell proliferation, or on the survival of proliferating cells, but may also have an effect on other cellular activities.

As used herein, the term "antiodorant agent" refers to any agent that stops or inhibits odorant perception by an animal. Said perception may be assayed using animal studies, ex vivo or in vitro studies simulating or representative for in vivo odorant perception. Examples of odorant perceptions may be, but are not limited to, aldehyde, fruity light, fruity dark, sweet aromatic, balsamic, aromatic spicy, tobacco, oakmoss, leather, animal, amber, woody, coniferous, herbal spicy, herbaceous, green, citrus.

With the expression "dysregulation of RCC356 activity" is meant that the activity of RCC356 may not be performed compared to a normal condition in which said receptor resides. Said dysregulation may result from a condition in which the RCC356 receptor is not stimulated correctly by a RCC356 specific ligand or from a condition in which the stimulation of RCC356 is transmitted in a different way to the signalling molecules compared to the wild type RCC356 receptor.

With the expression "method of diagnosing" is meant a method by which a disease or disorder may be detected, in said situation there exists already measurable indications or signs for the presence and/or development of said disease or disorder in the patient.

With the expression "method of prognosing" is meant a method by which the possibility to develop a disease or disorder is measured, in said situation there exists no or nearly invisible indications or signs for the presence and/or development of said disease or disorder in the patient.

With "isovaleric equivalent" is meant a molecule which has the same or comparable effect compared to isovaleric acid. Examples of said equivalent are listed above, but are not limited to said compound. The description provides enough information, in combination with the common general knowledge, so that a skilled person may determine if a compound may be considered as an isovaleric equivalent or not. A general formula for such "isovaleric equivalent" may be $(CH3)_x$—$(CH2)_y$—$(CH)_z$—COOH. In addition, different radicals containing different chemical function including but not limited to amine, ketone, ester, ether and alcohol may be grafted to said general formula.

BRIEF DESCRIPTION OF THE FIGURES

FIG. 1: Sequences of RCC356. cDNA sequence and translated amino acid sequence coding for full length coding region of RCC356 are shown. Said sequences have been previously disclosed in U.S. Pat. No. 6,790,631.

FIG. 3 A shows efficiency of the different identified ligands on RCC356 activation expressed as a percent of forskolin response. FIG. 3 B-D shows results of concentration-response analysis performed with citric, butyric, isovaleric, valeric, caproic, oenanthylic, caprilic, pelargonic, hexahydrobenzoic and 5-hexenoic acids on RCC356-overexpressing Hek293 cells.

FIG. 4 A: Recording of fluorescence variation induced upon injection of 250 μM of isovaleric acid on cells loaded with fluo4-AM, a calcium tracer, and expressing RCC356. Cells were observed with a magnification of 20×. Timescale is expressed in seconds. Isovaleric acid was injected 10 seconds after record started. B: Measurement of fluorescence. Each trace on the graph represents fluorescence intensity measured in one cell of the observed field. The vertical bar drawn at 10 seconds indicates the injection time.

FIG. 5 A: Recording of fluorescence variation induced upon injection of 250 μM of butyric acid on cells loaded with fluo4-AM, a calcium tracer, and expressing RCC356. Cells were observed with a magnification of 20×. Timescale is expressed in seconds. Butyric acid was injected 10 seconds after record started. B: Measurement of fluorescence. Each trace on the graph represents fluorescence intensity measured in one cell of the observed field. The vertical bar drawn at 10 seconds indicates the injection time.

FIG. 6 A: Recording of fluorescence variation induced upon injection of 500 μM of pelargonic acid on cells loaded with fluo4-AM, a calcium tracer, and expressing RCC356. Cells were observed with a magnification of 20×. Timescale is expressed in seconds. Pelargonic acid was injected 10 seconds after record started. B: Measurement of fluorescence. Each trace on the graph represents fluorescence intensity measured in one cell of the observed field. The vertical bar drawn at 10 seconds indicates the injection time.

DETAILED DESCRIPTION OF THE INVENTION

Figure 2:
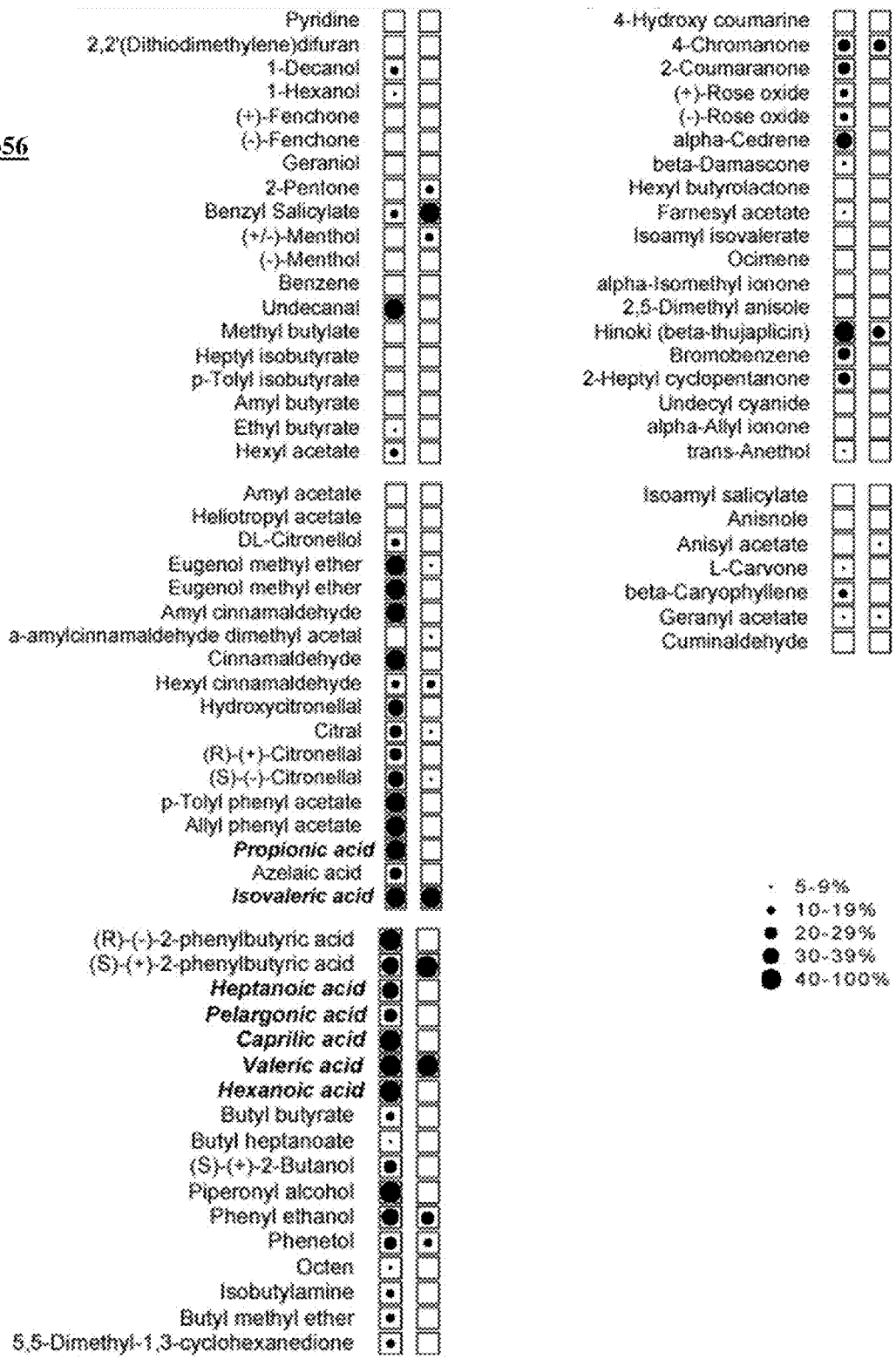
FIG. 2: Results of screening 80 ligands tested on RCC356 overexpressed in Hek293T. Results are expressed as percent of forskolin activation.

The invention relates to the discovery that isovaleric acid is a natural ligand for said RCC356 GPCR. The interaction is useful for screening assays for agents that modulate the interaction and thus the function of RCC356. The known ligand and its interaction with the receptor also provides for the diagnosis of conditions involving dysregulated said receptor activity.

I. Assays for the Identification of Agents that Modulate the Activity of RCC356

Agents that modulate the activity of RCC356 can be identified in a number of ways that take advantage of the interaction of said receptor with isovaleric acid. For example, the ability to reconstitute RCC356/isovaleric acid binding either in vitro, on cultured cells or in vivo provides a target for identification of agents that disrupt that binding. Assays based on disruption of binding can identify agents, such as small organic molecules, from libraries or collections of such molecules. Alternatively, such assays can identify agents in samples or extracts from natural sources, including plant, fungal or bacterial extracts or even human tissue samples. Modulators of RCC356/isovaleric acid binding can then be screened using a binding assay or a functional assay that measures downstream signaling through the said receptor. Both binding assays and functional assays are validated using isovaleric acid.

Another approach that uses the RCC356/isovaleric acid interaction more directly to identify agents that modulate RCC356 function measures changes in RCC356 downstream signaling induced by candidate agents or candidate modulators. These functional assays can be performed in isolated cell membrane fractions or on cells expressing the receptor on their surfaces.

The following description provides methods for both binding and functional assays based upon the interaction of RCC356 and isovaleric acid.

A. RCC356 Polypeptides.

Assays using the interaction of RCC356 and isovaleric acid require a source of RCC356 polypeptide. The polynucleotide and polypeptide sequence of human RCC356 are presented herein in FIG. 1. The human RCC356 polynucleotide sequence is also available at GenBank Accession No. AR581085.1, and was reported in U.S. Pat. No. 6,790,631 incorporated herein by reference. RCC356 polypeptide sequence is also recorded at accession Nos. sp|Q8TCB6|oxe1-human in the Swissprot database. Related sequences include those NM_152430, NP_689643, AY775731, AAV54110.1, AB065787, BAC06006, BK004369, DAA04767, AC090719, AL833127, AY698056, AAU07996.

One skilled in the art can readily amplify a RCC356 sequence from a sample containing mRNA encoding the protein through basic PCR and molecular cloning techniques using primers or probes designed from the known sequences. Also, since OR gene are intronless gene, one skilled person in the art can amplify RCC356 sequence from genomic DNA.

The expression of recombinant polypeptides is well known in the art. Those skilled in the art can readily select vectors and expression control sequences for the expression of RCC356 polypeptides useful according to the invention in eukaryotic or prokaryotic cells. RCC356 must be associated with cell membrane or detergents like synthetic liposomes in order to have binding or signaling function. Methods for the preparation of cellular membrane fractions are well known in the art, e.g., the method reported by Hubbard & Cohn, 1975, J. Cell Biol. 64: 461-479, which is incorporated herein by reference. In order to produce membranes comprising RCC356, one need only to apply such techniques to cells endogenously or recombinantly expressing RCC356. Alternatively, membrane-free RCC356 can be integrated into membrane preparations by dilution of detergent solution of the polypeptide (see, e.g., Salamon et al., 1996, Biophys. J. 71:283-294, which is incorporated herein by reference).

B. Isovaleric Acid.

The structure of isovaleric acid is well known by a skilled person. In addition, the skilled in the art may easily derive equivalent acids from said structure and may easily test if said equivalents are able to bind and/or modulate the RCC356 receptor. Isovaleric acids and equivalents thereof may be isolated from natural samples, or chemically synthesized.

Methods which can be used to quantify said acids may be, but are not limited to, a) for extraction and purification: solvent extraction, oil extraction, vapour extraction, $CO_2$ supercritical extraction, liquid chromatography, distillation, gas chromatography; b) for quantifying: gas chromatography, liquid chromatography and mass spectrometry. A skilled person knows how to perform said methods.

Isovaleric acid or its equivalents may be used in purified form or used as composition. The amounts of the acid necessary in a given binding or functional assay according to the invention will vary depending upon the assay, but will generally use 0.1 µM to 100 µM of labeled and 10 µM to 1 mM of unlabeled acid per assay. The affinities and $EC_{50}$s of modified isovaleric acid molecules for RCC356 may vary relative to those of the original isovaleric acid, and the amount necessary for a given assay can therefore be adjusted relative to the normal values. If necessary for a given assay, isovaleric acid can be labeled by incorporation or addition of radiolabeled labels as pointed above.

C. Assays to Identify Modulators of RCC356 Activity

The discovery that isovaleric acid is a ligand of the RCC356 receptor permits screening assays to identify agonists, antagonists and inverse agonists of receptor activity. The screening assays will have two general approaches.

1) Ligand binding assays, in which cells expressing RCC356, membrane extracts from such cells, or immobilized lipid membranes comprising RCC356 are exposed to a labeled isovaleric acid and candidate compound. Following incubation, the reaction mixture is measured for specific binding of the labeled isovaleric acid to the RCC356 receptor. Compounds that interfere with or displace labeled isovaleric acid can be agonists, antagonists or inverse agonists of RCC356 activity. Functional analysis can be performed on positive compounds to determine which of these categories they fit.

Binding of a compound may be classified in 3 main categories: competitive binding, non-competitive binding and uncompetitive binding. A competitive binding compound resembles a second (reference) compound and binds to the same binding pocket of a target molecule (here receptor). Upon addition, the competitive binding compound displaces said second compound from said target. A non-competitive binding compound does not bind to the same binding pocket of the target molecule as a second (reference) compound but may interact with the effect of said second compound on said target molecule. The second compound is not displaced upon addition of the non-competitive binding compound. An uncompetitive-binding compound binds to the target molecule when a second compound is already bound. Cooperative binding means that a compound facilitates the binding of another compound which may be a reference compound. The cooperative effect is thus seen in the analysis of the Kd of said other compound.

2) Functional assays, in which a signaling activity of RCC356 is measured.

a) For agonist screening, cells expressing RCC356 or membranes prepared from them are incubated with candidate compound, and a signaling activity of RCC356 is measured. The assays are validated using isovaleric acid as agonist, and the activity induced by compounds that modulate receptor activity is compared to that induced by isovaleric acid. An agonist or partial agonist will have a maximal biological activity corresponding to at least 10% of the maximal activity of isovaleric acid when the agonist or partial agonist is present at 100(0) µM or less, and preferably will have 50%, 75%, 100% or more, including 2-fold, 5-fold, 10-fold or more activity than isovaleric acid.

b) For antagonist or inverse agonist screening, cells expressing RCC356 or membranes isolated from them are assayed for signaling activity in the presence of isovaleric acid with or without a candidate compound. Antagonists or inverse agonists will reduce the level of isovaleric acid-stimulated receptor activity by at least 10%, relative to reactions lacking the antagonist or inverse agonist.

c) For inverse agonist screening, cells expressing constitutive RCC356 activity or membranes isolated from them are used in a functional assay that measures an activity of the receptor in the presence and in the absence of a candidate compound. Inverse agonists are those compounds that reduce the constitutive activity of the receptor by at least 10%. Overexpression of RCC356 may lead to constitutive activation. RCC356 can be overexpressed by placing it under the control of a strong constitutive promoter, e.g., the CMV early promoter. Alternatively, certain mutations of conserved GPCR amino acids or amino acid domains tend to lead to constitutive activity. See for example: Kjelsberg et al., 1992, J. Biol. Chem. 267:1430; McWhinney et al., 2000. J. Biol. Chem. 275:2087; Ren et al., 1993, J. Biol. Chem. 268:16483; Samama et al., 1993, J. Biol. Chem. 268:4625; Parma et al., 1993, Nature 365:649; Parma et al., 1998, J. Pharmacol. Exp. Ther. 286:85; and Parent et al., 1996, J. Biol. Chem. 271: 7949.

Ligand Binding and Displacement Assays:

One can use RCC356 polypeptides expressed on a cell, or isolated membranes containing receptor polypeptides, along with isovaleric acid in order to screen for compounds that inhibit the binding of isovaleric acid to RCC356. When identified in an assay that measures binding or isovaleric acid displacement alone, compounds will have to be subjected to functional testing to determine whether they act as agonists, antagonists or inverse agonists.

For displacement experiments, cells expressing a RCC356 polypeptide (generally 25,000 cells per assay or 1 to 100 µg of membrane extracts) are incubated in binding buffer (e.g., 50 mM Hepes pH 7.4; 1 mM $CaCl_2$; 0.5% Bovine Serum Albumin (BSA) Fatty Acid-Free; and 0.5 mM $MgCl_2$) for 1.5 hrs (at, for example, 27° C.) with labeled isovaleric acid in the presence or in the absence of increasing concentrations of a candidate modulator. To validate and calibrate the assay, control competition reactions using increasing concentrations of unlabeled isovaleric acid can be performed. After incubation, cells are washed extensively, and bound, labeled isovaleric acid is measured as appropriate for the given label (e.g., scintillation counting, enzyme assay, fluorescence, etc.). A decrease of at least 10% in the amount of labeled isovaleric acid bound in the presence of candidate modulator indicates displacement of binding by the candidate modulator. Candidate modulators are considered to bind specifically in this or other assays described herein if they displace 50% of labeled isovaleric acid (sub-saturating isovaleric acid dose) at a concentration of 100 µM or less (i.e., $EC_{50}$ is 100 µM or less).

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of isovaleric acid from the aqueous phase to a RCC356 polypeptide immobilized in a membrane on the sensor. This change in mass is measured as resonance units versus time after injection or removal of isovaleric acid or candidate modulator and is measured using a Biacore Biosensor (Biacore AB). RCC356 can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for isovaleric acid binding to RCC356 in an SPR assay can be fine-tuned by one of skill in the art using the conditions reported by Sarrio et al. as a starting point.

SPR can assay for modulators of binding in at least two ways. First, isovaleric acid can be pre-bound to immobilized RCC356 polypeptide, followed by injection of candidate modulator at approximately 10 µl/min flow rate and a concentration ranging from 1 nM to 1000 µM, preferably about 100 µM. Displacement of the bound isovaleric acid can be quantitated, permitting detection of modulator binding. Alternatively, the membrane-bound RCC356 polypeptide can be pre-incubated with candidate modulator and challenged with isovaleric acid. A difference in isovaleric acid binding to the RCC356 exposed to modulator relative to that on a chip not preexposed to modulator will demonstrate binding. In either assay, a decrease of 10% or more in the amount of isovaleric acid bound is in the presence of candidate modulator, relative to the amount of isovaleric acid bound in the absence of candidate modulator indicates that the candidate modulator inhibits the interaction of RCC356 and isovaleric acid. Biacore system can be plugged to a system identifying candidate modulator such as mass spectrometry, or gas chromatography.

Another method of measuring inhibition of binding of isovaleric acid to RCC356 uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g., isovaleric acid and a RCC356 polypeptide, are labeled with a complementary pair of donor and acceptor fluorophores. While close to each other due to RCC356: isovaleric acid interaction, fluorescence emitted upon excitation of the donor fluorophore will have a different wavelength than that emitted in response to that excitation wavelength when the molecules are not bound, providing for quantitation of bound versus unbound polypeptides by measurement of emission intensity at each wavelength. Donor:Acceptor pairs of fluorophores with which to label the target molecules are well known in the art.

A variation on FRET uses fluorescence quenching to monitor molecular interactions. One molecule in the interacting pair can be labeled with a fluorophore, and the other with a molecule that quenches the fluorescence of the fluorophore when brought into close apposition with it. A change in fluorescence upon excitation is indicative of a change in the association of the molecules tagged with the fluorophore: quencher pair. Generally, an increase in fluorescence of the labeled RCC356 polypeptide is indicative that isovaleric acid bearing the quencher has been displaced. For quenching assays, a 10% or greater increase in the intensity of fluorescent emission in samples containing a candidate modulator, relative to samples without the candidate modulator, indicates that the candidate modulator inhibits RCC356: isovaleric acid interaction.

Bioluminescence Resonance Energy Transfer (BRET) is a system for monitoring intermolecular interactions in vivo. The assay is based on non-radiative energy transfer between fusion proteins containing *Renilla* luciferase (Rluc) and e.g. Yellow Fluorescent Protein (YPF) or Green Fluorescent Protein (GFP). The BRET signal is generated by the oxidation of a coelenterazine derivative substrate. Said system may apply a cell-permeable and non-toxic coelenterazine derivative substrate DeepBleuC™ (DBC) and a mutant of the Green Fluorescent Protein (GFP) as acceptor. When the donor and acceptor are in close proximity the energy resulting from the catalytic degradation of the DBC is transferred from Rluc to GFP which will then emit fluorescence as its characteristic wavelength. This method allows higher distance between the two tested molecules and is fluorophore-angle independent.

In addition to the surface plasmon resonance and FRET and BRET methods, fluorescence polarization measurement is useful to quantitate isovaleric acid-receptor binding. The fluorescence polarization value for a fluorescently-tagged molecule depends on the rotational correlation time or tumbling rate. Protein complexes, such as those formed by RCC356 associating with a fluorescently labeled isovaleric acid, have higher polarization values than uncomplexed, labeled isovaleric acid. The inclusion of a candidate inhibitor of the RCC356:isovaleric acid interaction results in a decrease in fluorescence polarization, relative to a mixture without the candidate inhibitor, if the candidate inhibitor disrupts or inhibits the interaction of RCC356 with isovaleric acid. Fluorescence polarization is well suited for the identification of small molecules that disrupt the formation of polypeptide or protein complexes. A decrease of 10% or more in fluorescence polarization in samples containing a candidate modulator, relative to fluorescence polarization in a sample lacking the candidate modulator, indicates that the candidate modulator inhibits RCC356: isovaleric acid interaction.

Another alternative for monitoring RCC356: isovaleric acid interactions uses a biosensor assay. ICS biosensors have been described by AMBRI (Australian Membrane Biotechnology Research Institute; http//www.ambri.com.au/). In this technology, the association of molecules such as RCC356 and isovaleric acid, is coupled to the closing of gramacidin-facilitated ion channels in suspended membrane bilayers and thus to a measurable change in the admittance (similar to impedence) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of RCC356 and isovaleric acid.

It is important to note that in assays of acid-protein interaction, it is possible that a modulator of the interaction need not necessarily interact directly with the domain(s) of the proteins that physically interact. It is also possible that a modulator will interact at a location removed from the site of acid-protein interaction and cause, for example, a conformational change in the RCC356 polypeptide. Modulators (inhibitors or agonists) that act in this manner are nonetheless of interest as agents to modulate the activity of RCC356.

Any of the binding assays described can be used to determine the presence of an agent in a sample, e.g., a tissue sample, that binds to the RCC356 receptor molecule, or that affects the binding of isovaleric acid to the receptor. To do so, RCC356 polypeptide is reacted with isovaleric acid or another ligand in the presence or in the absence of the sample, and isovaleric acid or ligand binding is measured as appropriate for the binding assay being used. A decrease of 10% or more in the binding of isovaleric acid or other ligand indicates that the sample contains an agent that modulates isovaleric acid or ligand binding to the receptor polypeptide.

Proteins Chips

The methods of the present invention may be applied on protein chips. Said protein chip may be, but is not limited to, a glass slide or a nitrocellulose membrane. Array-based methods for protein chips are well known in the art.

Functional Assays of Receptor Activity i. GTPase/GTP Binding Assays:

For GPCRs such as RCC356, a measure of receptor activity is the binding of GTP by cell membranes containing receptors. In the method described by Traynor and Nahorski, 1995, Mol. Pharmacol. 47: 848-854, incorporated herein by reference, one essentially measures G-protein coupling to membranes by measuring the binding of labeled GTP. For GTP binding assays, membranes isolated from cells expressing the receptor are incubated in a buffer containing 20 mM HEPES, pH 7.4, 100 mM NaCl, and 10 mM $MgCl_2$, 80 pM $^{35}$S-GTPγS and 3 µM GDP. The assay mixture is incubated for 60 minutes at 30° C., after which unbound labeled GTP is removed by filtration onto GF/B filters. Bound, labeled GTP is measured by liquid scintillation counting. In order to assay for modulation of isovaleric acid-induced RCC356 activity, membranes prepared from cells expressing a RCC356 polypeptide are mixed with isovaleric acid, and the GTP binding assay is performed in the presence and in the absence of a candidate modulator of RCC356 activity. A decrease of 10% or more in labeled GTP binding as measured by scintillation counting in an assay of this kind containing candidate modulator, relative to an assay without the modulator, indicates that the candidate modulator inhibits RCC356 activity.

A similar GTP-binding assay can be performed without isovaleric acid to identify compounds that act as agonists. In this case, isovaleric acid-stimulated GTP binding is used as a standard. A compound is considered an agonist if it induces at least 50% of the level of GTP binding induced by isovaleric acid when the compound is present at 1 mM or less, and preferably will induce a level the same as or higher than that induced by isovaleric acid.

GTPase activity is measured by incubating the membranes containing a RCC356 polypeptide with $γ^{32}$P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing RCC356 (mock-transfected), in order to exclude possible non-specific effects of the candidate compound.

In order to assay for the effect of a candidate modulator on RCC356-regulated GTPase activity, membrane samples are incubated with isovaleric acid, with and without the modulator, followed by the GTPase assay. A change (increase or decrease) of 10% or more in the level of GTP binding or GTPase activity relative to samples without modulator is indicative of RCC356 modulation by a candidate modulator.

ii. Downstream Pathway Activation Assays:

a. Calcium Flux—The Aequorin-based Assay.

The aequorin assay takes advantage of the responsiveness of mitochondrial or cytoplasmic apoaequorin to intracellular calcium release or calcium flux (entrance) induced by the activation of GPCRs (Stables et al., 1997, Anal. Biochem. 252:115-126; Detheux et al., 2000, J. Exp. Med., 192 1501-1508; both of which are incorporated herein by reference). Briefly, RCC356-expressing clones are transfected to coexpress mitochondrial or cytoplasmic apoaequorin and Gα16 or G-olf. Cells are incubated with 5 µM Coelenterazine H or derivates (Molecular Probes) for 4 hours at room temperature, washed in DMEM-F12 culture medium and resuspended at a concentration of $0.5 \times 10^6$ cells/ml. Cells are then mixed with test agonist peptides and light emission by the aequorin is recorded with a luminometer for 30 sec. Results are expressed as Relative Light Units (RLU). Controls include assays using membranes isolated from cells not expressing C356 (mock-transfected), in order to exclude possible non-specific effects of the candidate compound.

Aequorin activity or intracellular calcium levels are "changed" if light intensity increases or decreases by 10% or more in a sample of cells, expressing a RCC356 polypeptide and treated with a candidate modulator, relative to a sample of cells expressing the C356 polypeptide but not treated with the candidate modulator or relative to a sample of cells not expressing the RCC356 polypeptide (mock-transfected cells) but treated with the candidate modulator.

When performed in the absence of isovaleric acid, the assay can be used to identify an agonist or inverse agonist of RCC356 activity. When the assay is performed in the presence of isovaleric acid, it can be used to assay for an antagonist.

1) a Fluo3, 4, Fura2, and Calcium3 (Molecular Device) Based-Assay.

Fluorescence-based assays take advantage of calcium fluxes triggered by receptor activation: either calcium entrance through CNG for instance or calcium release from endoplasmic reticulum. Some fluorophores including but not limited to Fluo3, Fluo4 and Fura2 (Molecular Probes) and Calcum3 kit series (Molecular Device) are known to bind calcium. Such fluorophore-calcium complexes emit fluorescence at respective specific wavelength. Thereby, upon activation of a G-protein coupled receptor, calcium released from endoplasmic reticulum or entered through CNG binds to fluorophore leading to specific fluorescence emission. RCC356-overexpressing cells are incubated for 30 to 60 minutes with a solution of 1 to 8 µM fluorophore at 37° C. After thorough washing with saline buffer, 50 µl of the same buffer is poored in each well-containing cells (6 to 1536). Tested agonists are then injected onto such loaded-cells and activation of RCC356 is followed by fluorescence measurement.

Intracellular calcium levels are "changed" if fluorescence intensity increases or decreases by 10% or more in a sample of cells, expressing a RCC356 polypeptide and treated with a candidate modulator, relative to a sample of cells expressing the C356 polypeptide but not treated with the candidate modulator or relative to a sample of cells not expressing the RCC356 polypeptide (mock-transfected cells) but treated with the candidate modulator.

2) Depolarization/Hyperpolarization Membrane Assay (DiBac Fluorophore for Instance).

The principle of this assay is to follow depolarization of cell membrane. The anionic probe $DiBAC_4(3)$ partitions between intra- and extracellular compartments in a membrane potential-dependent manner. With increasing membrane potential (depolarization), the probe further partition into the cell resulting in an increase of fluorescence. Conversely, hyperpolarization leads to a decrease of fluorescence due to a dye extrusion.

The $DiBAC_4(3)$ probe is excited with a wavelength of 488 nm, and emits at a wavelength of 540 nm.

On the day of the experiment, add the glucose to the assay buffer (saline buffer) to a final concentration of 10 mM and the DiBAC4(3) probe to a final concentration of 5 µM. Maintain the assay buffer at 37° C. Remove the cell culture medium and rinse twice each well containing RCC356-overexpressing cells with 200 µl of pre-heated assay buffer. Place 180 µl of Assay buffer containing DiBAC4(3) and incubate cells for 30 min at the appropriate temperature. Cell plates will be ready for assay after these 30 min incubation. Collect baseline for 2 min prior any addition. Add 20 µl of candidate modulators to the appropriate well and collect the data for an additional 25 min.

Membrane polarization is "changed" if fluorescence intensity increases or decreases by 10% or more in a sample of cells, expressing a RCC356 polypeptide and treated with a candidate modulator, relative to a sample of cells expressing the C356 polypeptide but not treated with the candidate modulator or relative to a sample of cells not expressing the RCC356 polypeptide (mock-transfected cells) but treated with the candidate modulator.

3) Melanophore assay. The melanophore assay is a color-based assay. Basically cells used for this assay are derived from skin of the frog *Xenopus Laevis*. These immortalized cells contained melanosomes, which are organelles containing dark pigment. Activation of endogenous or recombinant GPCR that trigger activation of adenylate cyclase or phospholipase C lead to melanosome dispersion and thereof cell darkening. Alternatively, GPCR that inhibits adenylate cyclase or phospholipase C leads to cell lightening. Thereby, instead of measuring concentrations of second messenger, one can easily pinpoint hit observing cell coloration change. This color change can easily be quantified on a microplate reader measuring absorbance at 650 nM or by examination on a video imaging system.

b. Adenylate Cyclase Assay:

Assays for adenylate cyclase activity are described by Kenimer & Nirenberg, 1981, Mol. Pharmacol. 20: 585-591, incorporated herein by reference. That assay is a modification of the assay taught by Solomon et al., 1974, Anal. Biochem. 58: 541-548, also incorporated herein by reference. Briefly, 100 µl reactions contain 50 mM Tris-Hcl (pH 7.5), 5 mM $MgCl_2$, 20 mM creatine phosphate (disodium salt), 10 units (71 µg of protein) of creatine phosphokinase, 1 mM $\alpha$-$^{32}$P-ATP (tetrasodium salt, 2 µCi), 0.5 mM cyclic AMP, G-3H-labeled cyclic AMP (approximately 10,000 cpm), 0.5 mM Ro20-1724, 0.25% ethanol, and 50-200 µg of protein homogenate to be tested (i.e., homogenate from cells expressing or not expressing a RCC356 polypeptide, treated or not treated with isovaleric acid with or without a candidate modulator). Reaction mixtures are generally incubated at 37° C. for 6 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The CAMP fraction from the column is eluted with 4 ml of 0.1 mM imidazole-HCl (pH 7.5) into a counting vial. Assays should be performed in triplicate. Control reactions should also be performed using protein homogenate from cells that do not express a RCC356 polypeptide.

Assays should be performed using cells or extracts of cells expressing RCC356, treated or not treated with isovaleric acid with or without a candidate modulator. Control reactions should be performed using mock-transfected cells, or extracts from them in order to exclude possible non-specific effects of some candidate modulators According to the invention, adenylate cyclase activity is "changed" if it increases or decreases by 10% or more in a sample taken from cells treated with a candidate modulator of RCC356 activity, relative to a similar sample of cells not treated with the candidate modulator or relative to a sample of cells not expressing the RCC356 polypeptide (mock-transfected cells) but treated with the candidate modulator. Alternatively, a decrease of activity by 10% or more by the candidate modulator of RCC356 in a sample treated with a reference compound may be tested.

c. cAMP Assay:

Intracellular CAMP is measured using a CAMP radioimmunoassay (RIA) or CAMP binding protein according to methods widely known in the art. For example, Horton & Baxendale, 1995, Methods Mol. Biol. 41: 91-105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

Assays should be performed using cells or extracts of cells expressing RCC356, treated or not treated with isovaleric acid with or without a candidate modulator. Control reactions should be performed using mock-transfected cells, or extracts from them in order to exclude possible non-specific effects of some candidate modulators The level of CAMP is "changed" if the level of CAMP detected in cells, expressing a RCC356 polypeptide and treated with a candidate modulator of RCC356 activity (or in extracts of such cells), using the RIA-based assay of Horton & Baxendale, 1995, supra, increases or decreases by at least 10% relative to the CAMP level in similar cells not treated with the candidate modulator.

d. Phospholipid Breakdown, DAG Production and Inositol Triphosphate Levels:

Receptors that activate the breakdown of phospholipids can be monitored for changes due to the activity of known or suspected modulators of RCC356 by monitoring phospholipid breakdown, and the resulting production of second messengers DAG and/or inositol triphosphate ($IP_3$). Methods of measuring each of these are described in Phospholipid Signaling Protocols, edited by Ian M. Bird. Totowa, N.J., Humana Press, 1998, which is incorporated herein by reference. See also Rudolph et al., 1999, J. Biol. Chem. 274: 11824-11831, incorporated herein by reference, which also describes an assay for phosphatidylinositol breakdown. Assays should be performed using cells or extracts of cells expressing RCC356, treated or not treated with isovaleric acid with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing a RCC356 polypeptide and treated with a candidate modulator in the presence or in the absence of isovaleric acid, relative to the level observed in a sample from cells expressing a RCC356 polypeptide that is not treated with the candidate modulator.

e. PKC Activation Assays:

Growth factor receptor tyrosine kinases tend to signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-NH2 (SEQ ID NO. 2), derived from the myristoylated alanine-rich protein kinase C substrate protein (MARCKS). The $K_m$ of the enzyme for this peptide is approximately 50 μM. Other basic, protein kinase C-selective peptides known in the art can also be used, at a concentration of at least 2-3 times their $K_m$. Cofactors required for the assay include calcium, magnesium, ATP, phosphatidylserine and diacylglycerol. Depending upon the intent of the user, the assay can be performed to determine the amount of PKC present (activating conditions) or the amount of active PCK present (non-activating conditions). For most purposes according to the invention, non-activating conditions will be used, such that the PKC that is active in the sample when it is isolated is measured, rather than measuring the PKC that can be activated. For non-activating conditions, calcium is omitted in the assay in favor of EGTA.

The assay is performed in a mixture containing 20 mM HEPES, pH 7.4, 1-2 mM DTT, 5 mM $MgCl_2$, 100 μM ATP, ~1 μCi $\gamma$-$^{32}$P-ATP, 100 μg/ml peptide substrate (~100 μM), 140 μM/3.8 μM phosphatidylserine/diacylglycerol membranes, and 100 μM calcium (or most preferably 500 μM EGTA). 48 μl of sample, diluted in 20 mM HEPES, pH 7.4, 2 mM DTT is used in a final reaction volume of 80 μl. Reactions are performed at 30° C. for 5-10 minutes, followed by addition of 25 μl of 100 mM ATP, 100 mM EDTA, pH 8.0, which stops the reactions.

After the reaction is stopped, a portion (85 μl) of each reaction is spotted onto a Whatman P81 cellulose phosphate filter, followed by washes: four times 500 ml in 0.4% phosphoric acid, (5-10 min per wash); and a final wash in 500 ml 95% EtOH, for 2-5 min. Bound radioactivity is measured by scintillation counting. Specific activity (cpm/nmol) of the labeled ATP is determined by spotting a sample of the reaction onto P81 paper and counting without washing. Units of PKC activity, defined as nmol phosphate transferred per min, are calculated as follows:

The activity, in UNITS (nmol/min) is:

$$= \frac{(cpm \text{ on paper}) \times (105 \ \mu l \text{ total}/85 \ \mu l \text{ spotted})}{(\text{assay time, min})(\text{specific activity of } ATP \ cpm/\text{nmol})}.$$

An alternative assay can be performed using a Protein Kinase C Assay Kit sold by PanVera (Cat. # P2747).

Assays are performed on extracts from cells expressing a RCC356 polypeptide, treated or not treated with isovaleric acid with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing RCC356 and treated with a candidate modulator, relative to a reaction performed on a similar sample from cells not treated with a candidate modulator.

f. PKA Activation Assays

PKA activity can be assayed using any of several kits available commercially, for example from molecular device IMAP PKA assay kit, or from promega ProFluor PKA assay kit.

Assays should be performed using cells or extracts of cells expressing RCC356, treated or not treated with isovaleric acid with or without a candidate modulator. Control reactions should be performed using mock-transfected cells, or extracts from them in order to exclude possible non-specific effects of some candidate modulators PKA activity is "changed" if the level of activity is increased or decreased by 10% or more in a sample from cells, expressing a RCC356 polypeptide, treated with a candidate modulator relative to PKA kinase activity in a sample from similar cells not treated with the candidate modulator.

g. Kinase Assays:

MAP kinase activity can be assayed using any of several kits available commercially, for example, the p38 MAP Kinase assay kit sold by New England Biolabs (Cat # 9820) or the FlashPlate™ MAP Kinase assays sold by Perkin-Elmer Life Sciences.

Assays should be performed using cells or extracts of cells expressing RCC356, treated or not treated with isovaleric acid with or without a candidate modulator. Control reactions should be performed using mock-transfected cells, or extracts from them in order to exclude possible non-specific effects of some candidate modulators MAP Kinase activity is "changed" if the level of activity is increased or decreased by 10% or more in a sample from cells, expressing a RCC356 polypeptide, treated with a candidate modulator relative to MAP kinase activity in a sample from similar cells not treated with the candidate modulator.

Direct assays for tyrosine kinase activity using known synthetic or natural tyrosine kinase substrates and labeled phosphate are well known, as are similar assays for other types of kinases (e.g., Ser/Thr kinases). Kinase assays can be performed with both purified kinases and crude extracts prepared from cells expressing a RCC356 polypeptide, treated with or without isovaleric acid, with or without a candidate modulator. Control reactions should be performed using mock-transfected cells, or extracts from them in order to exclude possible non-specific effects of some candidate modulators. Substrates can be either full length protein or synthetic peptides representing the substrate. Pinna & Ruzzene (1996, Biochem. Biophys. Acta 1314: 191-225, incorporated herein by reference) list a number of phosphorylation substrate sites useful for measuring kinase activities. A number of kinase substrate peptides are commercially available. One that is particularly useful is the "Src-related peptide," (RRLIEDAEYMRG (SEQ ID NO. 1); available from Sigma # A7433), which is a substrate for many receptor and nonreceptor tyrosine kinases. Because the assay described below requires binding of peptide substrates to filters, the peptide substrates should have a net positive charge to facilitate binding. Generally, peptide substrates should have at least 2 basic residues and a free amino terminus. Reactions generally use a peptide concentration of 0.7-1.5 mM.

Assays are generally carried out in a 25 µl volume comprising 5 µl of 5× kinase buffer (5 mg/mL BSA, 150 mM Tris-Cl (pH 7.5), 100 mM $MgCl_2$; depending upon the exact kinase assayed for, $MnCl_2$ can be used in place of or in addition to the $MgCl_2$), 5 µl of 1.0 mM ATP (0.2 mM final concentration), γ-32P-ATP (100-500 cpm/pmol), 3 µl of 10 mM peptide substrate (1.2 mM final concentration), cell extract containing kinase to be tested (cell extracts used for kinase assays should contain a phosphatase inhibitor (e.g. 0.1-1 mM sodium orthovanadate)), and $H_2O$ to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spun for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated 32P is measured by scintillation counting. The specific activity of ATP in the kinase reaction (e.g., in cpm/pmol) is determined by spotting a small sample (2-5 µl) of the reaction onto a P81 filter circle and counting directly, without washing. Counts per minute obtained in the kinase reaction (minus blank) are then divided by the specific activity to determine the moles of phosphate transferred in the reaction.

Assays should be performed using cells or extracts of cells expressing RCC356, treated or not treated with isovaleric acid with or without a candidate modulator. Control reactions should be performed using mock-transfected cells, or extracts from them in order to exclude possible non-specific effects of some candidate modulators.

Tyrosine kinase activity is "changed" if the level of kinase activity is increased or decreased by 10% or more in a sample from cells, expressing a RCC356 polypeptide, treated with a candidate modulator relative to kinase activity in a sample from similar cells not treated with the candidate modulator.

h. Transcriptional Reporters for Downstream Pathway Activation:

The intracellular signal initiated by binding of an agonist to a receptor, e.g., RCC356, sets in motion a cascade of intracellular events, the ultimate consequence of which is a rapid and detectable change in the transcription and/or translation of one or more genes. The activity of the receptor can therefore be monitored by measuring the expression of a reporter gene driven by control sequences responsive to RCC356 activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, Chloramphenicol Acetyl Transferase (CAT), Green Fluorescent Protein (GFP), β-lactamase or β-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful to make reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The c-fos regulatory elements include (see, Verma et al., 1987, Cell 51: 513-514): a TATA box that is required for transcription initiation; two upstream elements for basal transcription, and an enhancer, which includes an element with dyad symmetry and which is required for induction by phorbol ester 12-O-tetradecanoylphorbol-β-acetate (TPA), serum, Epidermal Growth Factor (EGF), and PMA.

The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is, as the name implies, responsive to levels of intracellular cAMP. Therefore, the activation of a receptor that signals via modulation of cAMP levels can be monitored by measuring either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., 1988, Proc. Natl. Acad. Sci. 85:6662-6666); the somatostatin gene promoter (cAMP responsive; Montminy et al., 1986, Proc. Natl. Acad. Sci. 8.3:6682-6686); the proenkephalin promoter (responsive to cAMP, nicotinic agonists, and phorbol esters; Comb et al., 1986, Nature 323:353-356); the phosphoenolpyruvate carboxy-kinase (PEPCK) gene promoter (cAMP responsive; Short et al., 1986, J. Biol. Chem. 261:9721-9726).

Additional examples of transcriptional control elements that are responsive to changes in GPCR activity include, but are not limited to those responsive to the AP-1 transcription factor and those responsive to NF-κB activity. The consensus AP-1 binding site is the palindrome TGA(C/G)TCA (Lee et al., 1987, Nature 325: 368-372; Lee et al., 1987, Cell 49: 741-752). The AP-1 site is also responsible for mediating induction by tumor promoters such as the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include, but are not limited to the genes for Fos and Jun (which proteins themselves make up AP-1 activity), Fos-related antigens (Fra) 1 and 2, IκBα, ornithine decarboxylase, and annexins I and II.

The NF-κB binding element has the consensus sequence GGGGACTTTCC (SEQ ID NO. 3). A large number of genes have been identified as NF-κB responsive, and their control elements can be linked to a reporter gene to monitor GPCR activity. A small sample of the genes responsive to NF-κB includes those encoding IL-1β (Hiscott et al., 1993, Mol. Cell. Biol. 13: 6231-6240), TNF-α (Shakhov et al., 1990, J. Exp. Med. 171: 35-47), CCR5 (Liu et al., 1998, AIDS Res. Hum. Retroviruses 14: 1509-1519), P-selectin (Pan & McEver, 1995, J. Biol. Chem. 270: 23077-23083), Fas ligand (Matsui et al., 1998, J. Immunol. 161: 3469-3473), GM-CSF (Schreck & Baeuerle, 1990, Mol. Cell. Biol. 10: 1281-1286) and IκBα (Haskill et al., 1991, Cell 65: 1281-1289). Each of these references is incorporated herein by reference. Vectors encoding NF-κB-responsive reporters are also known in the art or can be readily made by one of skill in the art using, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct should be tested by exposing RCC356-expressing cells, transfected with the construct, to isovaleric acid. An increase of at least two-fold in the expression of reporter in response to isovaleric acid indicates that the reporter is an indicator of RCC356 activity.

In order to assay RCC356 activity with isovaleric acid-responsive transcriptional reporter construct, cells that stably express RCC356 polypeptide are stably transfected with the reporter construct. To screen for agonists, untreated cells are exposed to candidate modulators, or exposed to isovaleric acid, and expression of the reporter is measured. The isovaleric acid-treated cultures serve as a standard for the level of transcription induced by a known agonist. An increase of at least 10% in reporter expression in the presence of a candidate modulator compare to reporter expression in the absence of any modulator indicates that the candidate is a modulator of RCC356 activity. An agonist will induce at least as much, and preferably the same amount or more reporter expression than the isovaleric acid. Partial agonists may activate the receptor less compared to isovaleric acid. This approach can also be used to screen for inverse agonists where cells express a RCC356 polypeptide at levels such that there is an elevated basal activity of the reporter in the absence of isovaleric acid or other agonists. A decrease in reporter activity of 10% or more in the presence of a candidate modulator, relative to its absence, indicates that the compound is an inverse agonist.

To screen for antagonists, the cells expressing RCC356 and carrying the reporter construct are exposed to isovaleric acid (or another agonist) in the presence and absence of candidate modulator. A decrease of 10% or more in reporter expression in the presence of candidate modulator, relative to the absence of the candidate modulator, indicates that the candidate is a antagonist of RCC356 activity.

Controls for transcription assays include cells not expressing RCC356 but carrying the reporter construct, as well as cells with a promoterless reporter construct. Compounds that are identified as modulators of RCC356-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening chemical libraries of chemical compounds for those that modulate RCC356 activity. The libraries can be, for example, libraries from natural sources, e.g., plants, animals, bacteria, etc., or they can be libraries comprising randomly or systematically equivalents of isovaleric acid.

i. Receptor Internalization

Any of the assays of receptor activity, including calcium flux, membrane polarization, melanophore assay, the GTP-binding, GTPase, adenylate cyclase, cAMP, phospholipid-breakdown, diacylglyceorl, inositol triphosphate, PKC, PKA, kinase, receptor internalization and transcriptional reporter assays, can be used to determine the presence of an agent in a sample, e.g., a tissue sample, that affects the activity of the RCC356 receptor molecule. To do so, RCC356 polypeptide is assayed for activity in the presence and in the absence of the sample or an extract of the sample. An increase in RCC356 activity in the presence of the sample or extract relative to the absence of the sample indicates that the sample contains an agonist of the receptor activity. A decrease in receptor activity in the presence of isovaleric acid or another agonist and the sample, relative to receptor activity in the presence of isovaleric acid alone, indicates that the sample contains an antagonist of RCC356 activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. One exception is the transcriptional reporter assay, in which at least a two-fold increase or 10% decrease in signal is necessary for a sample to be said to contain a modulator. It is preferred that an agonist stimulates at least 50%, and preferably 75% or 100% or more, e.g., 2-fold, 5-fold, 10-fold or greater receptor activation than isovaleric acid.

Other functional assays include, for example, microphysiometer or biosensor assays (see Hafner, 2000, *Biosens. Bioelectron.* 15: 149-158, incorporated herein by reference).

II. Diagnostic Assays Based Upon the Interaction of RCC356 and Isovaleric Acid:

Isovaleric acid is an unpleasant smelling organic acid forming part of the malodour formation of human and animal secretions, particular of sweat. As said acid and other odorants were found to modulate the RCC356 receptor, the present invention suggests that RCC356 probably also has an olfactory function. The present invention thus suggests that odor-recognition, in particular mediated by isovaleric acid, and equivalent acids thereof, may be modulated through the modulation of RCC356. Ligands recognizing RCC356 such as isovaleric acid may thus be used to influence at least isovaleric acid-related odor perception. Based on said finding, diagnostic assays may be set up to determine if malfunctioning RCC356 receptors are present in a subject, which leads to a deprived odor recognition.

Signaling through GPCRs is instrumental in the pathology of a large number of diseases and disorders. RCC356 is expressed in many tissues including prostate and has been shown to act as an indicator for cancer progression of such tissues (U.S. Pat. No. 6,790,631). Said cancer may be prostate, cervix, uterus, rectum, stomach and kidney cancer. Therefore, besides its role in olfaction, RCC356 has most likely a role to play in cancer processus. Progression and/or treatment of said cancers may be studied using the methods of the present invention. For instance assays described in the present invention may be set up using isovaleric acid, isovaleric acid equivalents or isovaleric acid-antibodies.

There are some evidences that RCC356 is expressed in the brain (BBRC 2003, Vanti et al. 305: 67-71). However, its role in CNS disorders or diseases has not yet been revealed. In addition, it has been previously suggested that isovaleric acid could be involved in epilepsy treatment (Epilepsia, 2004 45:1338-43). In fact valerian extract and most particularly powdered valerian roots is well known as anticonvulsive. Besides it has been shown that isovaleric acid was a constituent of such powder. One can thus assume that isovaleric acid may have anticonvulsant properties. Based on the findings of the present invention that isovaleric acid is a natural ligand of RCC356, the present invention suggests that, RCC356 could be seen as a target to treat CNS disorders, in particular epilepsy. However, the present invention does not exclude that said receptors may also be involved in migraine, vomiting, psychotic and neurological disorders, including anxiety, schizophrenia, manic depression, depression, delirium, dementia and severe mental retardation, neurodegenerative diseases such as Alzheimer's disease or Parkinson's disease, and dyskinasias, such as Huntington's disease or Gilles de la Tourett's syndrome and other related diseases. The provision of isovaleric acid as ligand for RCC356, may help to elucidate said role. In addition, the present invention relates to the use of kits comprising reagents to quantify RCC356 or study RCC356 to diagnose CNS related diseases, in particular epilepsy.

The interaction of RCC356 with isovaleric acid can be used as the basis of assays for the diagnosis or monitoring of diseases, disorders or processes involving RCC356 signaling. Diagnostic assays for RCC356-related diseases or disorders can have several different forms.

First, diagnostic assays can quantify isovaleric acid in a tissue sample. Second, assays can evaluate the difference in binding of isovaleric acid on RCC356 in a tissue sample. Third, the presence of isovaleric acid (quantitative or qualitative) in a sample may be determined using a specific antibody recognizing isovaleric acid or isovaleric acid/RCC356 complex. The use of this antibody may be combined with the use of an antibody recognizing RCC356 specifically. Said methods may be used to diagnose CNS disorders or diseases and cancer progression, and treatments thereof.

In addition, the present invention suggests for the first time that RCC356 may play a role in odor perception and CNS disorders. Assays to diagnose or monitor olfactory malfunctioning or CNS disorders can have several forms.

First, antibodies to RCC356, to isovaleric acid or related acids, or to isovaleric acid/RCC356 complex may be applied in binding assays to measure the content of the RCC356 polypeptide in tissues. Second, RCC356 mRNA levels may be determined indicating the level of expression of the RCC356 gene. Finally, the mRNA or genomic DNA encoding RCC356 may be amplified and checked on sequence variations compared to the wild type RCC356 messenger or gene. The presence of variations may indicate the presence or predestination for olfactory disfunctions or CNS disorders.

According to the present method, said RCC356 polypeptide may be a polypeptide having at least 20% identity or higher identity, such as 25%, 30%, 35%, 40%, 45%, 55%, 65%, 75%, 85%, 95% or even 100% to the polypeptide represented in FIG. 1b. Alternatively, said RCC356 polypeptide may be a fragment of the full length polypeptide of said sequence, wherein the fragment retains at least 50% of the binding activity and level of signaling activation induced by isovaleric acid. According to the present invention, said RCC356 polypeptide may comprise one or more additions, insertions, deletions or substitutions relative to the wild type sequence as long as it has similar binding properties towards isovaleric acid. Said RCC356 polypeptide may a truncated RCC356 polypeptide; said RCC356 polypeptide may comprise additional sequences forming a RCC356 fusion protein, wherein said additional sequences may be chosen from the group consisting of glutathione-S-transferase (GST), maltose binding protein (MBP), alkaline phosphatase, thioredoxin, green fluorescent protein (GFP), histidine tags (e.g., 6× or greater His), or affinity tags (e.g., Myc tag, FLAG tag) sequences.

A. Assays to Quantify Small Organic Acids

Methods which can be used to quantify said acids may be, but are not limited to, a) for extraction and purification: solvent extraction, oil extraction, vapour extraction, CO2 supercritical extraction, liquid chromatography, distillation, gas chromatography; b) for quantifying: gas chromatography, liquid chromatography and mass spectrometry. A skilled person know how to perform said methods.

B. Assays that Measure the Amount or Variation of RCC356

RCC356 levels can be measured and compared to standards in order to determine whether an abnormal level of said receptor is present in a sample, i.e. more or less than in a standard tissue, either of which indicates probable dysregulation of RCC356 signaling. Polypeptide levels are measured, for example, by immunohistochemistry using antibodies specific for the polypeptide. A sample isolated from an individual suspected of suffering from a disease or disorder characterized by RCC356 activity is contacted with an antibody for RCC356, and binding of the antibody is measured as known in the art (e.g., by measurement of the activity of an enzyme conjugated to a secondary antibody).

Another approach to the measurement of RCC356 polypeptide levels uses flow cytometry analysis of cells from an affected tissue. Methods of flow cytometry, including the fluorescent labeling of antibodies specific for RCC356, are well known in the art. Other approaches include radioimmunoassay or ELISA. Methods for each of these are also well known in the art.

The amount of binding detected is compared to the binding in a sample of similar tissue from a healthy individual, or from a site on the affected individual that is not so affected. An increase of 10% or more relative to the standard is diagnostic for a disease or disorder characterized by RCC356 dysregulation.

RCC356 expression can also be measured by determining the amount of mRNA encoding said polypeptide in a sample of tissue. mRNA can be quantitated by quantitative or semi-quantitative PCR. Methods of "quantitative" amplification are well known to those of skill in the art, and primer sequences for the amplification of RCC356 are disclosed herein (U.S. Pat. No. 6,790,631). A common method of quantitative PCR involves simultaneously co-amplifying a known quantity of a control sequence using the same primers. This provides an internal standard that can be used to calibrate the PCR reaction. Detailed protocols for quantitative PCR are provided in 'PCR Protocols, A Guide to Methods and Applications', Innis et al., Academic Press, Inc. N.Y., (1990), which is incorporated herein by reference. An increase of 10% or more in the amount of mRNA encoding RCC356 in a sample, relative to the amount expressed in a sample of like tissue from a healthy individual or in a sample of tissue from an unaffected location in an affected individual is diagnostic for a disease or disorder characterized by dysregulation of RCC356 signaling.

C. Qualitative assays

Assays that evaluate whether or not the RCC356 polypeptide or the mRNA encoding it are wild-type or not can be used diagnostically. In order to diagnose olfactory dysfunction or CNS disorders or diseases characterized by RCC356 dysregulation in this manner, RNA isolated from a sample is used as a template for PCR amplification of RCC356. The amplified sequences are then either directly sequenced using standard methods, or are first cloned into a vector, followed by sequencing. A difference in the sequence that changes one or more encoded amino acids relative to the sequence of wild-type RCC356 can be diagnostic of a disease or disorder characterized by dysregulation of RCC356 signaling. It can be useful, when a change in coding sequence is identified in a sample, to express the variant receptor or ligand and compare its activity to that of wild type RCC356. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild-type and variant sequences: Hybridization assays that discriminate on the basis of changes as small as one nucleotide are well known in the art. Alternatively, any of a number of "minisequencing" assays can be performed, including, those described, for example, in U.S. Pat. Nos. 5,888,819, 6,004,744 and 6,013,431 (incorporated herein by reference). These assays and others known in the art can determine the presence, in a given sample, of a nucleic acid with a known polymorphism.

If desired, array or microarray-based methods can be used to analyze the expression or the presence of mutation, in RCC356 sequences. Array-based methods for minisequencing and for quantitation of nucleic acid expression are well known in the art.

D. Functional Assays.

Diagnosis of isovaleric acid-related olfactory malfunctioning or a CNS disease or disorder can also be performed using functional assays. To do so, cell membranes or cell extracts prepared from a tissue sample are used in an assay of RCC356 activity as described herein (e.g., ligand binding assays, calcium flux assays, membrane polarization assays, melanophore assay, GTP-binding assay, GTPase assay, adenylate cyclase assay, cAMP assay, phospholipid breakdown, diacyl glycerol or inositol triphosphate assays, PKC or PKA activation assay, kinase assay, or receptor internalization assay). The activity detected is compared to that in a standard sample taken from a healthy individual or from an unaffected site on the affected individual. As an alternative, a sample or extract of a sample can be applied to cells expressing RCC356, followed by measurement of RCC356 signaling activity relative to a standard sample. A difference of 10% or more in the activity measured in any of these assays, relative to the activity of the standard, is diagnostic for isovaleric acid-related olfactory malfunctioning or a CNS disease or disorder.

Modulation of RCC356 Activity expressed in a Cell According to the Invention

The discovery of isovaleric acid as a ligand of RCC356 provides methods of modulating the activity of a RCC356 polypeptide expressed in a cell. RCC356 activity is modulated in a cell by delivering to that cell an agent that modulates the function of RCC356 polypeptide. This modulation can be performed in cultured cells as part of an assay for the identification of additional modulating agents, or, for example, in an animal, including a human. Agents include isovaleric acid and equivalent acids thereof.

An agent can be delivered to a cell by adding it to culture medium. The amount to deliver will vary with the identity of the agent and with the purpose for which it is delivered. For example, in a culture assay to identify antagonists of RCC356 activity, one will preferably add an amount of isovaleric acid that half-maximally activates the receptors (e.g., approximately $EC_{50}$), preferably without exceeding the dose required for receptor saturation. This dose can be determined by titrating the amount of isovaleric acid to determine the point at which further addition of isovaleric acid has no additional effect on RCC356 activity.

When a modulator of RCC356 activity is administered as a medicament to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells, olfactory perception and CNS activities) is changed by at least 10% relative to the value for that aspect prior to treatment.

Candidate Modulators Useful According to the Invention

Candidate modulators can be screened from large libraries of synthetic or natural compounds. Numerous means are currently used for random and directed synthesis of various kinds of compounds. Synthetic compound libraries are commercially available from a number of companies including, for example, Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries of small organic molecules are available and can be prepared. Alternatively, libraries of natural compounds in the form of bacterial, fungal, plant and animal extracts are available from e.g., Pan Laboratories (Bothell, Wash.) or MycoSearch (NC), or are readily producable by methods well known in the art. Additionally, natural and synthetically produced libraries and compounds are readily modified through conventional chemical, physical, and biochemical means.

As noted previously herein, candidate modulators may be variants or equivalents of isovaleric acid. Therefore, a library of isovaleric acid-related compounds may be used. As shown by the results of the present invention (FIG. 3), isovaleric acid (iso structure) and valeric acid (linear structure) leads to similar Ec50, also from 4 to 9 carbone chains have been tested, all of them trigger RCC356 activation. Therefore, the present invention suggests that variants (or equivalents) of IVA can be made leading to compounds with comparable activity as IVA for RCC356. In particular, the present invention suggests possible variation playing with the alphatic chain length, from 2 carbones to 12 carbones for instance, playing with structure iso vs linear, also playing with the length of each radical chain of the isoversion, playing with the functional group both in the iso and linear form of the molecule (i.e.: carboxylic, aldehyde, alcohol, ester, ether . . . ), playing with the position of this functional group in both iso and linear structure.

Antibodies Useful According to the Invention

The invention relates to the specific use of antibodies to RCC356 and isovaleric acid and isovaleric acid/RCC356 complex. Antibodies can be made using standard protocols known in the art (See, for example, Antibodies: A Laboratory Manual ed. by Harlow and Lane (Cold Spring Harbor Press: 1988)). A mammal, such as a mouse, hamster, goat, sheep or rabbit, or a bird such as chicken can be immunized with an immunogenic form of the RCC356 peptide (e.g., a RCC356 polypeptide or an antigenic fragment which is capable of eliciting an antibody response, or a fusion protein as described herein above) or isovaleric acid, or isovaleric acid/RCC356 complex. Immunogens for raising antibodies are prepared by mixing the compounds (e.g., isolated recombinant polypeptides or synthetic peptides) with adjuvants. Alternatively, RCC356 polypeptides or peptides are made as fusion proteins to larger immunogenic proteins. Polypeptides can also be covalently linked to other larger immunogenic proteins, such as keyhole limpet hemocyanin. Isovaleric acid can be made more immunogenic by chemically linking said peptides to said acid. Alternatively, plasmid or viral vectors encoding RCC356, or a fragment of these proteins, can be used to express the polypeptides and generate an immune response in an animal as described in Costagliola et al., 2000, J. Clin. Invest. 105:803-811, which is incorporated herein by reference. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies. Such engineered antibodies could be kept as phage display library. Engineered antibody recognizing RCC356, isovaleric acid and/or isovaleric acid/RCC356 complex could thus be isolated from that library using binding assays including Biacore technology.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with a isovaleric acid or and equivalent acid or RCC356 peptide or polypeptide or isovaleric acid/RCC356 complex, and monoclonal antibodies isolated from the media of a culture comprising such hybridoma cells.

The production of an antibody specific for RCC356 has been described in U.S. Pat. No. 6,790,631. Antibodies directed against isovaleric acid can easily be made using one of the above-mentioned prior art methods.

Transgenic Animals Useful According to the Invention

Transgenic animals expressing RCC356 or variants thereof are useful to study the signaling through RCC356, as well as for the study of drugs or agents that modulate the activity of RCC356. A transgenic animal is a non-human animal containing at least one foreign gene, called a transgene, which is part of its genetic material. Preferably, the transgene is contained in the animal's germ line such that it can be transmitted to the animal's offspring. A number of techniques may be used to introduce the transgene into an animal's genetic material, including, but not limited to, microinjection of the transgene into pronuclei of fertilized eggs and manipulation of embryonic stem cells (U.S. Pat. No. 4,873,191 by Wagner and Hoppe; Palmiter and Brinster, 1986, *Ann. Rev. Genet.*, 20:465-499; French Patent Application 2593827 published Aug. 7, 1987, all of which are incorporated herein by reference). Transgenic animals can carry the transgene in all their cells or can be genetically mosaic.

According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains. Transgenes can be constitutively expressed or can be tissue specific or even responsive to an exogenous drug, e.g., Tetracycline. A transgenic animal expressing one transgene can be crossed to a second transgenic animal expressing a second transgene such that their offspring will carry and express both transgenes.

Knock-Out Animals

Animals bearing a homozygous deletion in the chromosomal sequences encoding RCC356 or variants can be used to study the function of the receptor. Of particular interest is whether a knockout in genes responsible for isovaleric acid production and/or catabolism such as IVDHase has a distinct phenotype, in particular of cancer or CNS disorders, which may point to whether isovaleric acid is the only ligand that binds RCC356 or if it is a member of a family. Of further particular interest is the identification of the specific role of RCC356/isovaleric acid in specific physiological and/or pathological processes.

i. Standard Knock Out Animals

Knock out animals are non-human animals and are produced by the method of creating gene deletions with homologous recombination. This technique is based on the development of embryonic stem (ES) cells that are derived from embryos, are maintained in culture and have the capacity to participate in the development of every tissue in the animals when introduced into a host blastocyst. A knock out animal is produced by directing homologous recombination to a specific target gene in the ES cells, thereby producing a null allele of the gene. The technology for making knock-out animals is well described (see, for example, Huszar et al., 1997, *Cell*, 88:131; and Ohki-Hamazaki et al., 1997, *Nature*, 390:165, both of which are incorporated herein by reference). One of skill in the art can generate a homozygous RCC356 knockout animal or a animal genes with a knockout in one or more genes responsible for isovaleric acid production and/or catabolism (e.g., a mouse).

ii. Tissue Specific Knock Out

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue (Marth, 1996, *Clin. Invest.* 97: 1999). In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function (Sauer, 1998, *Methods*, 14:381). There are now many in vivo examples of this method, including, for instance, the inducible inactivation of mammary tissue specific genes (Wagner et al., 1997, *Nucleic Acids Res.*, 25:4323). One of skill in the art can therefore generate a tissue-specific knock-out animal in which RCC356 or isovaleric acid-related genes as mentioned above is homozygously eliminated in a chosen tissue or cell type.

Kits Useful According to the Invention

The invention provides kits useful for screening for modulators of RCC356 activity, as well as kits useful for diagnosis of diseases or disorders characterized by dysregulation of RCC356 signaling. Kits useful according to the invention can include an isolated RCC356 polypeptide (including a membrane- or cell-associated RCC356 polypeptide, e.g., on isolated membranes, cells expressing RCC356, or, on an SPR chip) and an isolated isovaleric acid. When cells included, said cell may be transformed with a polynucleotide encoding said RCC356. In a further embodiment, the kit according to the invention may contain a polynucleotide encoding a RCC356 polypeptide and isovaleric acid. All kits according to the invention will comprise the stated items or combinations of items and packaging materials therefor. Kits may also include instructions for use.

According to the present kit, said isovaleric acid may be an isovaleric acid-related agent having a capacity of binding and/or modulating the RCC356 receptor similar to isovaleric acid. Said related agents may be for instance propionic acid, butyric acid, isobutyric acid, valeric acid, hexanoic acid, isohexanoic acids, heptanoic acid, isoheptanoic acids, octanoic acid, isooctanoic acids, nonanoic acid, isononanoic acids, valproic acid, isovaleramide, caproic acid, oenanthylic acid, caprylic acid, hexahydrobenzoic acid, pelargonic acid and 5-hexenoic acid.

According to the present invention, said RCC356 polypeptide may be a polypeptide having at least 20% identity or higher identity, such as 25%, 35%, 45%, 55%, 65%, 75%, 85%, 95% or even 100% to the polypeptide represented in FIG. 1b; and which binds specifically isovaleric acid or equivalent acids. Alternatively, said RCC356 polypeptide may be a fragment of the full length polypeptide as shown in FIG. 1b, wherein the fragment retains at least 50% of the binding activity and level of signaling activation when using isovaleric acid. According to the present invention, said RCC356 polypeptide may comprise one or more additions, insertions, deletions or substitutions relative to the sequence depictured in FIG. 1b. Said RCC356 polypeptide may be a truncated RCC356 polypeptide; said RCC356 polypeptide may comprise additional sequences forming a RCC356 fusion protein, wherein said additional sequences may be chosen from the group consisting of glutathione-S-transferase (GST), maltose binding protein (MBP), alkaline phosphatase, thioredoxin, green fluorescent protein (GFP), histidine tags (e.g., 6× or greater His), or affinity tags (e.g., Myc tag, FLAG tag) sequences.

EXAMPLES

Example 1

Screening of 80 Odorants on RCC356

Hek293 cells were grown in MEM supplemented with decomplemented FBS at 37° C. under 5% CO2 and 90% humidity. Two days before screening, cells were plated onto 96-well plates (PDL coated plates, Becton-Dickinson). The day after, cells were transfected with a plasmid encoding RCC356 polypeptide along with 2 plasmides encoding firefly luciferase and renilla luciferase respectively. Firefly transcription was driven by a minimum promoter including the CREB-response element (CRE), whereas renilla luciferase was driven by CMV promoter, a strong constitutive promoter. Transfection was performed using lipofectamine 2000 reagent (Invitrogen). Transfected cells were let under standard culture conditions for a further 24 hours, and then process for functional assay.

Odorants were dissolved as 1M solutions in DMSO. They were then plated onto 96-well plates as 200 µM solutions in HBSS (Cambrex). DMSO represented thereby less than 1% (v/v) of the odorant solutions. Positive controls such as forskolin were included in odorant plates. Forskolin activates production of cAMP that in turn, through binding to CREB transcription factor triggers production of firefly luciferase, the reporter gene of the system. Detected luciferase activity in each well could be thereby expressed as a percent of forskolin response, allowing standardization thereon.

Functional assay was performed using Dual-Glo luciferase assay Kit according to manufacturer instructions (Promega).

FIG. 2 shows results obtained after two independent screenings of 80 odorants on Hek293 overexpressing RCC356 polypeptide. Many odorants seemed to lead to RCC356 activation including isovaleric, valeric, propionic, hexanoic, heptanoic, caprilic and pelargonic acids. Among these potential hits, only isovaleric and valeric acids are found in both screening.

Example 2

Concentration-response Analysis of 7 Odorants on Hek293 Cells Overexpressing RCC356 Polypeptide To further validate hits found during screenings of 80 odorants on RCC356 overexpressing-Hek293 cells, concentration-response analyses have been performed. Hek293 cells were grown in MEM supplemented with decomplemented FBS at 37° C. under 5% CO2 and 90% humidity. Two days before screening, cells were plated onto 96-well plates (PDL coated plates, Becton-Dickinson). The day after, cells were transfected with a plasmid encoding RCC356 polypeptide along with 2 plasmides encoding firefly luciferase and renilla luciferase respectively. Firefly transcription was driven by a minimum promoter including the CREB-response element (CRE), whereas renilla luciferase was driven by CMV promoter, a strong constitutive promoter. Transfection was performed using lipofectamine 2000 reagent (Invitrogen). Transfected cells were let under standard culture conditions for a further 24 hours, and then process for functional assay.

First, tested odorants (isovaleric, valeric, propionic, hexanoic, heptanoic, caprilic and pelargonic acids) were dissolved as 1M solutions in DMSO. They were then plated onto 96-well plates at different concentrations ranging from 0.1 µM to 1 mM in HBSS (Cambrex). DMSO represented thereby less than 1% (v/v) of the odorant solutions. Positive controls such as forskolin were included in odorant plates. Forskolin activates production of cAMP that in turn, through binding to CREB transcription factor triggers production of firefly luciferase, the reporter gene of the system. Detected luciferase activity in each well could be thereby expressed as a percent of forskolin response, allowing standardization thereon.

Functional assay was performed using Dual-Glo luciferase assay Kit according to manufacturer instructions (Promega).

Figure 3A:
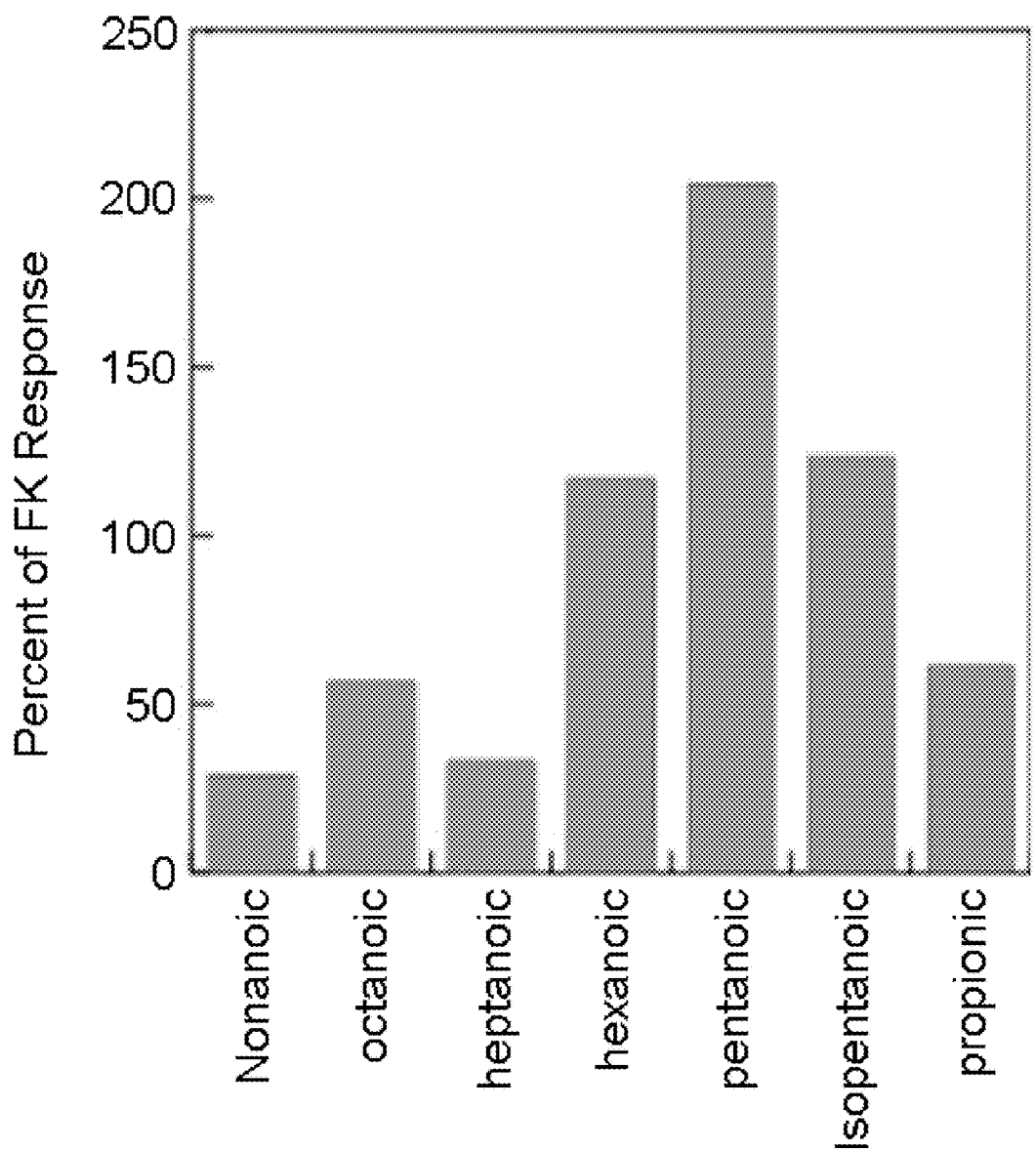
FIG. 3: Concentration response curves obtained after treatment of Hek293T overexpressing RCC356 with different agonists of the receptor.
Figure 3B:
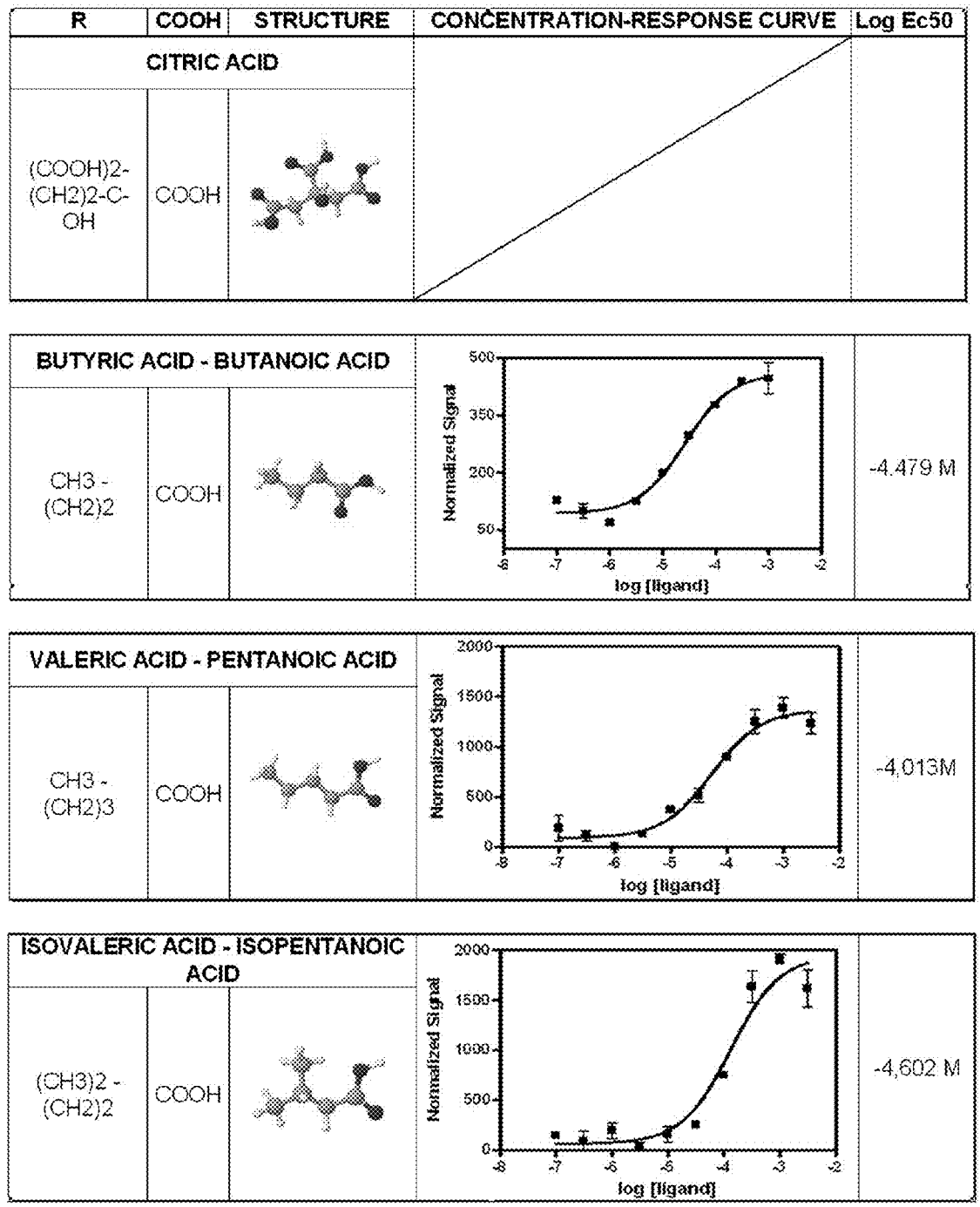
Figure 3C:
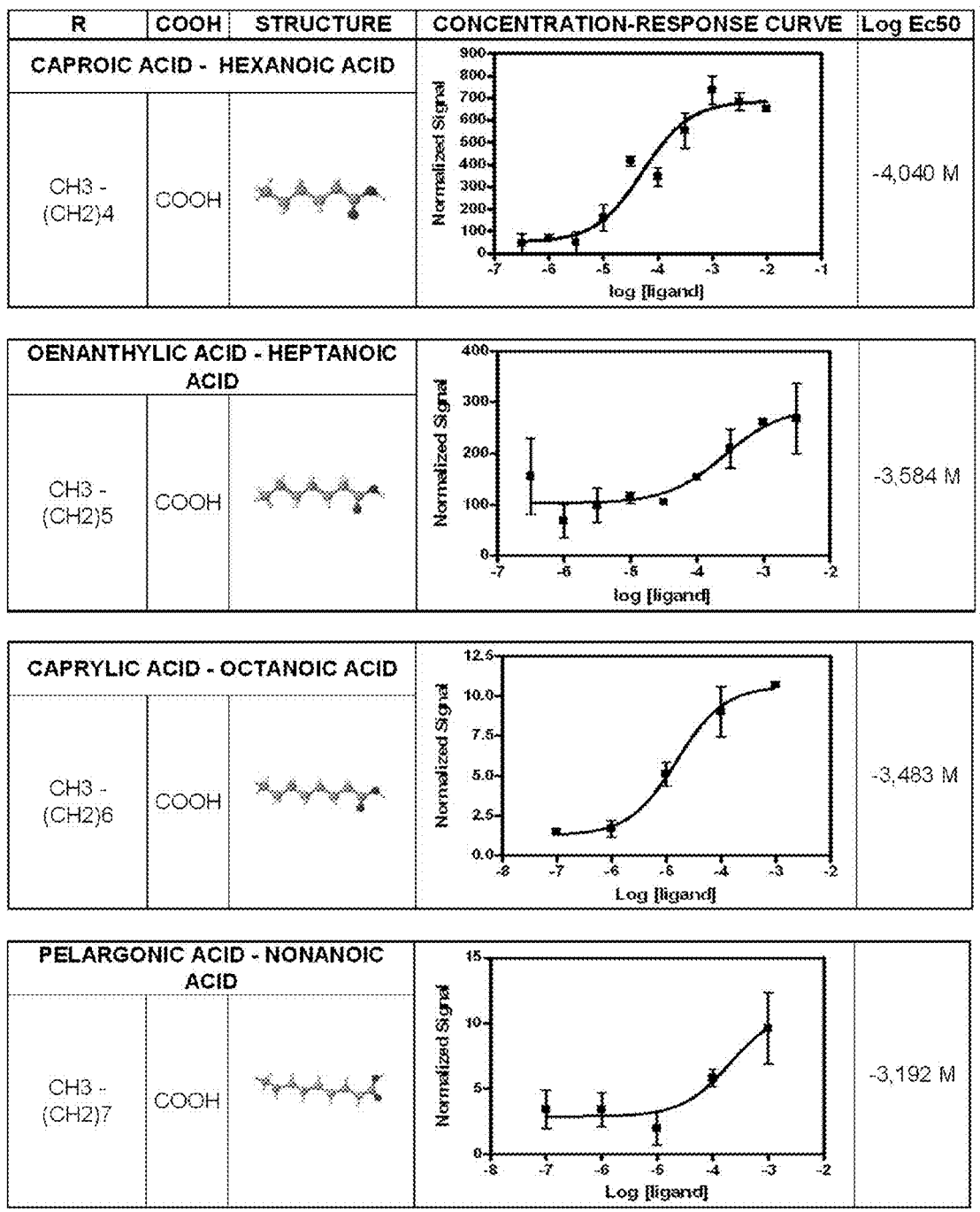

FIG. 3 A shows efficiency of the different identified ligands on RCC356 activation. FIG. 3 B-D shows results of concentration-response analysis performed with citric, butyric, isovaleric, valeric, caproic, oenanthylic, caprilic, pelargonic, hexahydrobenzoic and 5-hexenoic acids on RCC356-overexpressing Hek293 cells. Each of the tested hit is confirmed being ligand of RCC356. Among tested odorants, isovaleric acid is the most efficient ligand of RCC356 polypeptide. Isovaleric acid triggers RCC356 activation with an Ec50 of 25 µM. Valeric, caproic, oenanthylic, caprilic, pelargonic, hexahydrobenzoic and 5-hexenoic acids lead to RCC356 activation as well, with Ec50 of 97 µM, 91 µM, 260 µM, 329 µM, 643 µM, 104 µM and 485 µM, respectively.

Example 3

Single-cell Calcium-Imaging Assays Performed on Hek 293 Cells Overexpressing RCC356 Polypeptide For single-cell calcium imaging assay, cells were plated into 96 well-plates 48 h before the experiment and transfected with olfactory receptor cDNA 20 h prior calcium imaging assay, using lipofectamine (Invitrogen Inc.) according to manufacturer protocol. After a one hour-incubation at 37° C. in a saline buffer containing 4 µg/ml Fluo4-AM (Molecular Probe), cells were rinsed twice with Fluo4-AM-free saline buffer. 50 µl of saline buffer was added to each well. Calcium mobilization was recorded with a magnification of 20× on a Zeiss Axiovert 200 Mot microscope equipped for fluorescence detection. One image of the same field was taken each second during 60 seconds. 50 µl of the two fold concentrated ligand solubilised in the saline buffer was injected 10 seconds after record started. The ligands tested were isovaleric acid (FIG. 4), butyric acid (FIG. 5) and pelargonic acid (FIG. 6).

The invention claimed is:

1. A method of identifying an agent that binds to a RCC356 polypeptide, wherein said RCC356 polypeptide comprises SEQ ID NO: 5, said method comprising:
   a) contacting said RCC356 polypeptide with isovaleric acid in the presence or in the absence of a candidate modulator under conditions permitting the binding of said isovaleric acid to said RCC356 polypeptide; wherein said contacting is performed in or on a cell expressing said RCC356 polypeptide, performed in or on synthetic liposomes, or performed in or on virus-induced budding membranes containing said RCC356 polypeptide polypeptide, and
   b) measuring the binding of said RCC356 polypeptide to said isovaleric acid, wherein a decrease in binding in the presence of said candidate modulator, relative to the binding in the absence of said candidate modulator, identifies said candidate modulator as an agent that modulates the function of said RCC356 polypeptide.

2. The method according to claim 1, wherein said isovaleric acid is detectably labeled.

3. The method according to claim 2, wherein said acid is detectably labeled with a moiety selected from the group consisting of a radioisotope, a fluorophore, a quencher of fluorescence, and, an NMR-detectable moiety.

4. The method according to claim 1, wherein said method is performed using a membrane fraction from cells expressing said RCC356 polypeptide.

5. The method according to claim 1, wherein said method is performed on a protein chip.

6. The method according to claim 1, wherein said measuring is performed using a method selected from label displacement, surface plasmon resonance, fluorescence resonance energy transfer, fluorescence quenching, and fluorescence polarization.

7. The method according to claim 1, wherein said agent is selected from the group consisting of a peptide, a polypeptide, an antibody or antigen-binding fragment thereof, a lipid, a carbohydrate, a nucleic acid, and a small organic molecule.

8. The method according to claim 1, wherein said method is a high throughput screening method.

9. The method according to claim 1, wherein said agent is part of a chemical library or animal organ extracts.

10. The method according to claim 7, wherein said small organic molecule is an odorant compound or a pheromone.

11. The method of claim 1, wherein said isovaleric acid in claim 1 can be replaced by an acid selected from the group consisting of valeric, caproic, oenanthylic, caprilic, pelargonic, hexahydrobenzoic and 5-hexenoic acid.

* * * * *